(12) United States Patent
Bayley et al.

(10) Patent No.: US 6,426,231 B1
(45) Date of Patent: Jul. 30, 2002

(54) ANALYTE SENSING MEDIATED BY ADAPTER/CARRIER MOLECULES

(75) Inventors: Hagan Bayley; Orit Braha, both of College Station; LiQun Gu, Bryan, all of TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 09/441,376

(22) Filed: Nov. 17, 1999

Related U.S. Application Data
(60) Provisional application No. 60/109,034, filed on Nov. 18, 1998.

(51) Int. Cl.$^7$ .............................................. G01N 33/543
(52) U.S. Cl. ........................ 436/518; 204/400; 204/403; 422/55; 422/58; 422/82.01; 422/82.05; 422/82.08; 422/82.07; 435/287.1; 435/287.2; 435/288.7; 435/808; 436/517; 436/528; 436/536; 436/149; 436/805; 436/806; 530/391.1
(58) Field of Search .................................. 436/518, 501, 436/517, 536, 805, 806, 149, 528; 435/287.1, 287.2, 183, 288.7, 808; 530/391.1; 422/55, 58, 82.01, 82.05, 82.07, 82.08; 204/400, 403

(56) References Cited
U.S. PATENT DOCUMENTS

| | | | | |
|---|---|---|---|---|
| 5,252,743 A | * | 10/1993 | Barrett et al. | 548/303.7 |
| 5,620,850 A | * | 4/1997 | Bamdad et al. | 530/300 |
| 5,744,305 A | * | 4/1998 | Fodor et al. | 435/6 |
| 5,817,771 A | | 10/1998 | Bayley et al. | 435/183 |
| 5,824,776 A | | 10/1998 | Bayley et al. | 530/350 |
| 6,083,763 A | * | 7/2000 | Balch | 436/518 |

FOREIGN PATENT DOCUMENTS
WO    WO 99/05167    2/1999

OTHER PUBLICATIONS

Ekin et al. (1991). Multianalyte microspot immunoassay–microanalytical "compact disk" of the future. Clin. Chem. 37(11):1955–1966.*
Fodor et al. (1993). Multiplexed biochemical assays with biological chips. Nature. 364:555–556.*
He et al. (1997). Voltametric responsive sensors for organic compounds based on organized self–assembled lipoyl–b–cyclodextrin derivative monolayer on a gold electrode. Anal. Chim. Acta. 337:217–223.*
Nagase et al. (1990). Voltammetric anion responsive sensors based on modulation of ion permeability through Langmuir–Blodgett films containing synthetic anion receptors. Anal. Chem. 62:1252–1259.*
Bugler et al. (1998). Novel water–soluble b–cyclodextrin–calix[4]arene couples as fluorescent sensor molecules for the detection of neutral analytes. J. Org. Chem. 63:5339–5344.*

Kemeny (1997). Enzyme–linked immunoassays. In Immunochemistry 1, A Practical Approach (Eds. Johnstone et al.). New York: Oxford University Press, pp. 147–176.*
Gu, L. et al., "Stochastic sensing of organic analytes by a pore–forming protein containing a molecular adapter," Nature, vol. 398, pp. 686–690 (Apr. 1999).
Braha O., et al., "Designed protein pores as components for biosensors," Chemistry & Biology, vol. 4, pp. 497–505 (Jul. 1997).
Kasianowicz, et al., "Characterization of individual polynucleotide molecules using a membrane channel," Proc. Natl. Acad. Sci. USA, vol. 93, pp. 13770–13773 (Nov. 1996).
Krasilnikov, et al., "A simple method for the determination of the pore radius of ion channel sin planar lipid bilayer membranes," FEMS Microbiology Immunology, vol. 105, pp. 93–100 (1992).
Beer, et al., "Molecular recognition of anions by synthetic receptors," Current Opinion in Chemical Biology, vol. 1, pp. 475–482 (1997).
Chen, et al, "Recognition of neutral species with synthetic receptors," Current Opinion in Chemical Biology, vol. 1, pp. 458–466 (1997).
Hellinga, et al., "Protein engineering and the development of generic biosensors," Tibtech, vol. 16, pp. 183–189 (Apr. 1998).
Braha, et al., "Designated protein pores as components for biosensors," Chemistry & Biology, vol. 4, No. 7, pp. 497–505 (1997).
Bianchet, et al., "The three–dimensional structure of bovine odorant binding protein and its mechanism of odor recognition," Nature Structural Biology, vol. 3, No. 11, pp. 934–939 (Nov. 1996).
Xie, "Single–Molecule Spectroscopy and Dynamics at Room Temperature," Acc. Chem. Res., vol. 29, No. 12, pp. 598–606 (1996).
Hulteen, et al., "Introducing Chemical Transport Selectivity into Gold Nanotubule Membranes," J. Am. Chem. Soc., vol. 120, pp. 6603–6604 (1998).
Tabushi, et al., "A,B,D,F–Tetrasubstituted β–Cyclodextrin as Artificial Channel Compound," Tetrahedron Letters, vol. 23, No. 44, pp. 4601–4604 (1982).
Pregel, et al., "Towards Artificial Ion Channels: Transport of Alkali Metal Ions across Lipsomal Membranes by "Bouquet" Molecules," Angew. Chem. Int. Ed. Engl., vol. 31, No. 12, pp. 1637–1639 (1992).
Odashima, et al., "Voltammetric Study on a Condensed Monolayer of a Long Alkyl Cyclodextrin Derivative as a Channel Mimetic Sensing Membrane," Analytical Chemistry, vol. 65, No. 7, pp. 927–936 (Apr. 1, 1993).

(List continued on next page.)

Primary Examiner—Christopher L. Chin
(74) Attorney, Agent, or Firm—Baker Botts L.L.P.

(57) ABSTRACT

This invention relates to an improved method and system for sensing of one or more analytes. A host molecule, which serves as an adapter/carrier, is used to facilitate interaction between the analyte and the sensor element. A detectable signal is produced reflecting the identity and concentration of analyte present.

39 Claims, 9 Drawing Sheets

OTHER PUBLICATIONS

Duax, et al., "Molecular Structure and Mechanisms of Action of Cyclie and Linear Ion Transport Antibiotics," *Biopolymers (Peptide Science)*, vol. 40, pp. 141–155 (1996).

Walker, et al., "Functional Expression of the α–Hemolysin of *Staphylococcus aureus* in Intact *Escherichia coli* and in Cell Lysates," *The Journal of Biological Chemistry*, vol. 267, No. 15, pp. 10902–10909 (1982).

Bayley, "Building Doors into Cells," *Scientific American*, pp. 62–67 (Sep. 1997).

Menestrina, "Ionic Channels Formed by *Staphylococcus aureus* Alpha–Toxin: Voltage–Dependent Inhibition by Divalent and Trivalent Cations," *J. Membrane Biol.*, vol. 90, pp. 177–190 (1986).

Bhakdi, et al., "Staphylococcal α–toxin: Oligomerization of hydrophilic monomers to form amphiphilic hexamers induced through contact with deoxycholate detergent micelles," *Proc. Natl. Acad. Sci. USA*, vol. 78, No. 9, pp. 5475–5479 (Sep. 1981).

Doleman, et al., "Trends in odor intensity for human and electronic noses: Relative roles of odorant vapor pressure vs. molecularity specific odorant binding," *Proc. Natl. Acad. Sci. USA*, vol. 95, pp. 5442–5447 (May 1998).

Czarnik, "A sense for landmines," *Nature*, vol. 394, pp. 417–418 (Jul. 30, 1998).

Oberhauser, et al., "The molecular elasticity of the extracellular matrix protein tenascin," *Nature*, vol. 393, pp. 181–185 (May 14, 1998).

Cornell, et al., "A biosensor that uses ion–channel switches," *Nature*, vol. 387, pp. 580–583 (Jun. 5, 1997).

Petosa, et al., "Crystal structure of the anthrax toxin protective antigen," *Nature*, vol. 385, pp. 833–838 (Feb. 27, 1997).

Song, et al., "Structure of Staphylococcal α–Hemolysin, a Heptameric Transmembrane Pore," *Science*, vol. 274, pp. 1859–1866 (Dec. 13, 1996).

Doyle, et al., "The Structure of the Potassium Channel: Molecular Basis of $K^+$ Conduction and Selectivity," *Science*, vol. 280, pp. 69–77 (Apr. 3, 1998).

Sackmann, "Supported Membranes: Scientific and Practical Applications," *Science*, vol. 271, pp. 43–48 (Jan. 5, 1996).

Hartgerink, et al., "Pept6ide Nanotubes and Beyond," *Chem. Eur. J.*, vol. 4, No. 8, pp. 1367–1732 (1998).

Pregel, et al., "Channel–type Molecular Structures. Part 4. Transmembrane Transport of Alkali–metal Ions by 'Bouquet' Molecules," *J. Chem Soc. Perkin Trans.*, vol. 12, pp. 417–426 (1995).

Heyse, et al., "Emerging techniques for investigating molecular interactions at lipid membranes," *Biochimica et Bioophysica Acta*, 85507, pp. 319–338 (1998).

Schuster, et al, "Self–assembled α–hemolysin pores in an S–layer–supported lipid bilayer," *Biochimica et Biophysica Acta* 1370, pp. 280–288 (1998).

Gouaux, "α–Hemolysin from *Staphylococcus aureus:* An Archetype of β–Barrel, Channel–Forming Toxins," *Journal of Structural Biology*, vol. 121, pp. 110–122 (1998).

Schmid, et al., "Porin mutants with new channel properties," *Protein Science*, vol. 7, pp. 1603–1611 (1998).

Bezrukov, et al., "Dynamics and Free Energy of Polymers Partitioning into a Nanoscale Pore," *Macromolecules*, vol. 29, pp. 8517–8522 (1996).

Rekharsky, et al., "Complexation Thermodynamics of Cyclodextrins," *Chem. Rev.*, vol. 98, pp. 1875–1917 (1998).

* cited by examiner

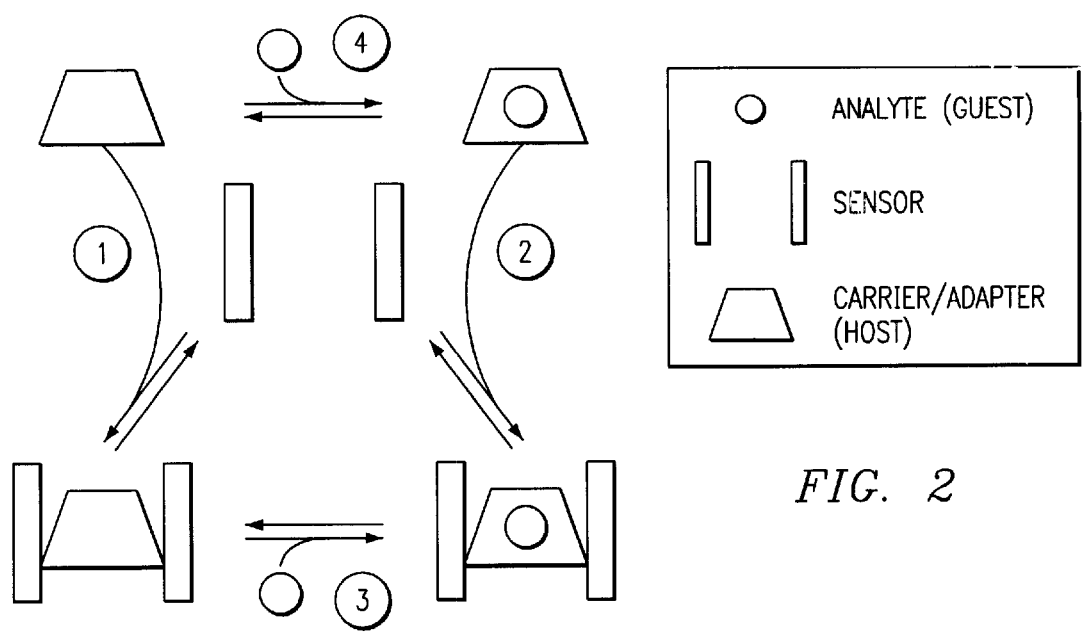
FIG. 2
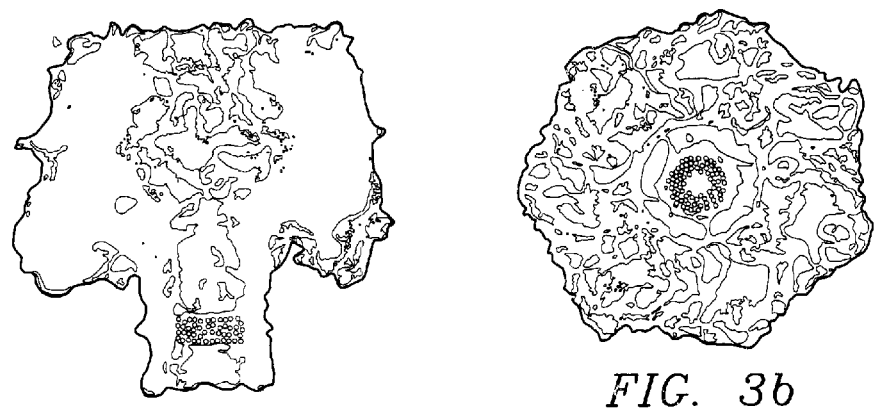
FIG. 3a
FIG. 3b
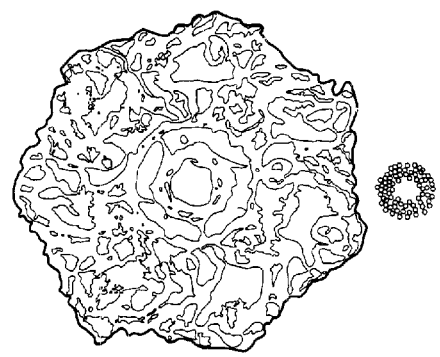
FIG. 3c

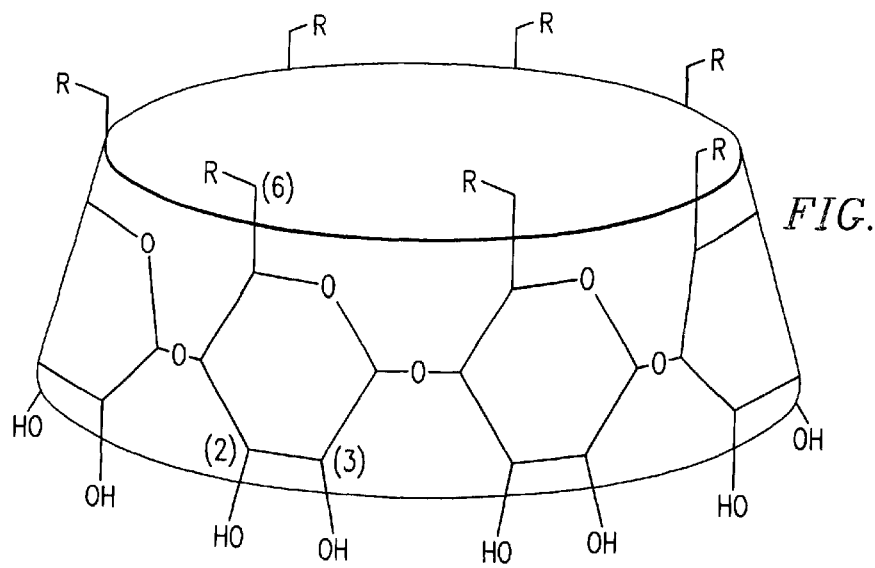
FIG. 7b
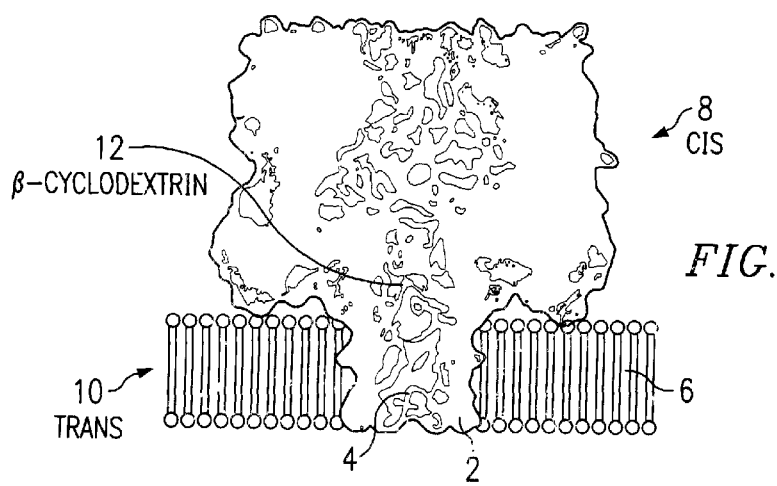
FIG. 7c
| 110K+ | 111E− | K+147 | Y148 | 110K+ | 111E− | K+148 | Y149 |
| 112Y | 113M | T145 | L146 | 112Y | 113M | T148 | L147 |
| 114S | 115T | G143 | H144 | 114S | 115T | G144 | H145 |
| 116L | 117T | S141 | I142 | 116L | 117T | S142 | L143 |
| 118Y | 119G | N139 | V140 | 118Y | 119E− | G140 | V141 |
| 120F | 121N | G137 | A138 | 120V | 121H | S138 | A139 |
| 122G | 123N | L135 | I136 | 122G | 123N | S136 | V137 |
| 124V | 125T | G133 | G134 | 124A | 125E− | G134 | G135 |
| 126G | 127D− | K+131 | I132 | 126V | 127H | D−132 | I133 |
| 128D− | | G130 | | 128A | | F131 | |
| | 129T | | | | 129S | F130 | |
FIG. 7d

ANALYTE SENSING MEDIATED BY ADAPTER/CARRIER MOLECULES

CROSS REFERENCE TO RELATED APPLICATIONS

This application claims the benefit of U.S. Provisional Patent Application No. 60/109,034, filed Nov. 18, 1998.

RIGHTS IN THE INVENTION

This invention was made in part with United States Government support under grants from DARPA, DOE, ONR, and the United States Government has certain rights in the invention.

BACKGROUND

1. Field of the Invention

This invention relates to the field of biosensing and, more particularly, to an improved method and system for analyte sensing mediated by adapter/carrier molecules which act as an adapter between the analyte and sensor element or deliver the analyte to the sensor element.

2. Description of the Background

Stochastic sensing is based on the detection of individual binding events between analyte molecules and a single receptor, which acts as a biosensor element. The read-out depends on a property of the receptor, usually a protein, that is altered when the binding site is occupied. In its simplest manifestation, stochastic sensing provides a binary signal (occupied/unoccupied) comprising fluctuations in, e.g. electrical current, fluorescence, or force. The frequency of occurrence of the binding events is determined by the concentration of the analyte. The nature of the binding events, e.g. the magnitude and duration of the associated signal, is determined by the properties of the analyte. The ability to identify an analyte by its characteristic signature is a distinctive feature of stochastic sensing.

The ability to observe changes in the state of single protein molecules has been available with respect to ion channels for over twenty years. The electrical currents generated by the large ion fluxes through these molecules (e.g., $10^8$ s$^{-1}$) can be monitored by single channel recording. More recently, structural changes in single protein molecules have been detected by fluorescence techniques and by force measurements (Doleman, B. J., et al., *Proc. Natl. Acad. Sci. USA* 95:5442–5447, 1998; Hellinga, H. W., et al., *Trends Biotechnol.* 16:183–189, 1998; Czarnik, A. W., *Nature* 394:417–418, 1998).

Genetically engineered versions of the bacterial pore forming protein α-Hemolysin (αHL) have been used as sensor elements. Current stochastic schemes are limited in that the type of analytes that can be sensed are restricted to those which interact with the pore. Current schemes cannot be used, for example, to analyze organic molecules, molecules insoluble in aqueous media and certain mixtures of analytes.

Better sensors would be useful in many situations. For example, in medicine, improved means for detecting physiological markers and therapeutic agents are needed; in environmental protection, various pollutants and effluents from factories must be monitored more thoroughly; for defense, new ways to detect explosives and chemical and biological agents are urgently required. In only a few cases are the available technologies optimal for the task at hand. Better devices are needed with improved sensitivity and rapid "real time" response.

There is therefore a need for analyte sensors, including stochastic biosensors, that can detect the presence and concentration of a wider variety of analytes as well as samples containing mixtures of analytes.

SUMMARY OF THE INVENTION

The present invention overcomes the problems and disadvantages associated with current strategies and designs and provides analyte sensing systems and methods which extend the categories of analytes that give a response and improve the dynamic range of response. A host molecule is used to serve as an adapter between the analyte and sensor element, or to deliver the analyte directly to the sensor element, producing a unique signal that indicates both the concentration and identity of the analyte. The invention is particularly useful in detecting organic molecules.

The present invention is a substantial improvement over stochastic sensing using pore proteins as sensor elements without the benefit of a host molecule. The host molecule of the present invention allows interactions between an analyte and a sensor element that would not normally occur. The host molecule of the present invention can concentrate analyte, even from the vapor phase. The host molecule may mediate the analysis of organic molecules that are normally insoluble in aqueous media. Two or more analyte molecules that interact with a host molecule can be analyzed simultaneously with a single sensor element. The complex signal can be resolved to reveal the concentrations of multiple components in a mixture. In addition, more than one host molecule can be used in combination with a single sensor element.

Accordingly, one embodiment of the invention is directed to a system for sensing at least one analyte comprising a sensor element and a host molecule. The sensor element has a receptor site. The host molecule, which acts as a carrier or adapter, is configured to interact with both the receptor site of the sensor element and the analyte to produce a detectable signal unique for the analyte.

Sensing may comprise identifying or quantitating/determining the concentration of the analyte, or both. The host molecule is preferably a cyclodextrin, such as β-cyclodextrin (βCD), and the sensor element is preferably an α-Hemolysin (αHL) pore.

Systems of the invention may be highly combinatorial. For example, another embodiment of the invention is directed to a system for sensing a plurality of different analytes comprising a plurality of different sensor elements, each sensor element comprising a pore and having a receptor site, and a plurality of different host molecules. The host molecules are each configured to interact with a receptor site of one of the plurality of different sensor elements and one of the different analytes to produce a detectable and unique signal.

Another embodiment of the invention is directed to a biosensor for detecting an analyte in a sample comprising a bilayer, which separates the biosensor into a first compartment and a second compartment, and a sensor element disposed in the first compartment so that it forms a channel in the bilayer. The biosensor further comprises a host molecule which is designed or configured to interact with a receptor site on the sensor element and the analyte to produce a detectable signal. The host molecule may be disposed in the first, second or both compartments.

Another embodiment of the invention is directed to a method for sensing at least one analyte in a sample comprising the steps of providing a biosensor, the biosensor comprising a sensor element having a receptor site and a host molecule, the host molecule configured to interact with the receptor site of the sensor element and the analyte to produce a detectable signal, allowing the sample to interact with the biosensor to produce a signal, and detecting the signal.

Still another embodiment of the invention is directed to a method of making a biosensor for detecting an analyte in a sample comprising providing a bilayer apparatus, the bilayer apparatus comprising a bilayer separating the apparatus into a first compartment and a second compartment, adding a sensor element to the first compartment and allowing it to form a channel in the bilayer, and providing a host molecule, the host molecule being configured to interact with a receptor site on the sensor element and the analyte to produce a detectable signal. The method further comprises the step of adding the host molecule to the first or second compartments or both. The host molecule may be added substantially simultaneously with the addition of the sample.

Another embodiment is directed to a method for modifying an interactive property of a protein with a second molecule comprising modifying the interactive property of the protein by contacting the protein with a third molecule, said third molecule comprising a non-covalent molecular adapter.

Other embodiments and advantages of the invention are set forth in part in the description which follows, and in part, will be obvious from this description, or may be learned from the practice of the invention.

DESCRIPTION OF THE DRAWINGS

FIG. 2 is a diagram illustrating the operation of the system according to a preferred embodiment of the present invention.

FIG. 3a is a molecular graphics representation of the interaction between αHL and βCD depicting a sagittal section through the pore with βCD lodged in the lumen of the transmembrane channel.

FIG. 3b is a molecular graphics representation of the interaction between αHL and βCD depicting a view into the channel from the trans side with βCD bound.

FIG. 3c is a molecular graphics representation of the interaction between αHL and βCD depicting a view into the channel from the trans side with βCD removed.

FIG. 5a is a diagram illustrating analysis of currents from binary solutions of analytes showing current amplitude histograms for a single αHL pore in the presence of βCD and 2-adamantanamine ($A_1$) and 1-adamantanecarboxylic acid ($A_2$).

FIG. 7b shows the structures of the β-cyclodextrins used in Examples 9–11.

FIG. 7c is a schematic of the WT-αHL pore showing βCD lodged in the lumen of the channel.

FIG. 7d shows sequences of the transmembrane β barrels in WT-αHL, (left) and αHL-CH1 (right).

DESCRIPTION OF THE INVENTION

Figure 1A:
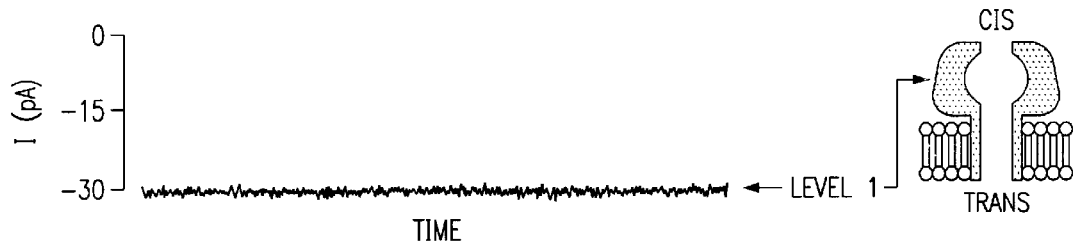
FIGS. 1a–d are bilayer recordings showing the interaction of a single αHL pore with βCD and the model analytes 2-adamantanamine ($A_1$) and 1-adamantanecarboxylic acid ($A_2$).
Figure 1B:
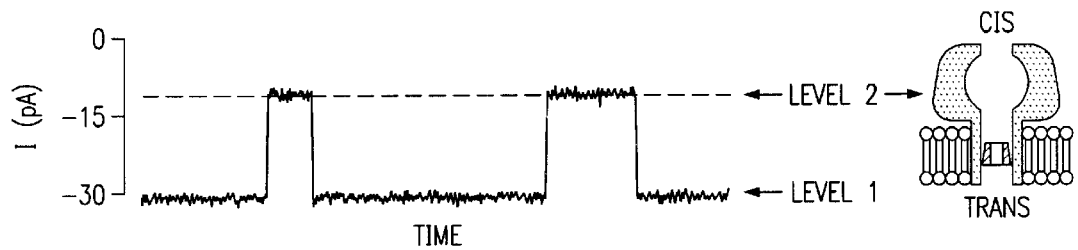

As embodied and broadly described herein, the present invention is directed to an improved method and system for analyte sensing mediated by carrier/adapter molecules. A host molecule is used to provide a binding site in the sensor element, thereby acting as an adapter between the sensor element and analyte, or to deliver the analyte directly to the sensor element. In either case, a unique signal is produced that indicates both the concentration and identity of the analyte.

In the adapter mode, the host molecule actually changes the binding properties of the sensor element, such as a protein, allowing it to interact with an analyte, such as an organic molecule, thereby facilitating detection of the analyte.

The present invention combines single molecule detection with protein engineering. Protein engineering allows the generation of an enormous variety of analyte binding sites in receptor macromolecules. Genetic engineering may be by design based on structural data, as well as by directed evolution by random or semi-random mutagenesis and gene shuffling. It also includes targeted chemical modification of proteins, enhanced by cutting-edge techniques in organic synthesis including combinatorial approaches.

Engineered transmembrane protein pores are useful sensor elements for stochastic detection (Braha, O., et al., *Chem. Biol.* 4:497–505, 1997). In their simplest manifestation, they produce a binary signal (occupied/unoccupied) comprising fluctuations in electrical current. The concentration of the analyte determines the frequency of occurrence of the fluctuations and, in a distinctive feature of stochastic sensing, the identity of the analyte is revealed by the "signature" of the binding events, e.g., the magnitude and duration of the current fluctuations.

Genetically engineered versions of the bacterial pore-forming protein α-hemolysin (αHL) have been used to identify and quantitate divalent metal ions in solution (Braha, O., et al., *Chem. Biol.* 4:497–505, 1997; also see U.S. patent application Ser. No. 09/122,583 filed Jul. 24, 1997, incorporated herein by reference). In one such study, the analyte binding site was placed in the lumen of the transmembrane channel. However, in this model it is likely that electrostatic effects, rather than steric block or a conformational change in the protein, were largely responsible for the modulation of current by analyte. As such, this strategy is of limited value in the detection of organic molecules, which may not necessarily be charged.

In contrast, the present invention allows for the detection of non-charged organic molecules. Analyte sensing using αHL equipped with a non-covalent molecular adapter according to the invention can be effectively used to distinguish and quantitate a variety of molecules, including organic molecules. Further, a single sensor element can be used to analyze mixtures of the analytes.

α-Hemolysin is an exotoxin secreted by *Staphylococcus aureus* (Gouaux, E., *J. Struct. Biol.* 121:110–122, 1998). The monomeric 293 amino acid polypeptide can self assemble on lipid bilayers to form a heptameric pore. The pore self assembles efficiently into bilayers either through the monomer (Menestrina, G., *J. Membrane Biol.*, 90:177–190, 1986) or as a preformed heptamer (Braha, O., et al., *Chem. Biol.*, 4:497–505, 1997). The pore is a mushroom-shaped structure in which the lower half of the stem, a 14-stranded β barrel, forms a transmembrane channel (Song, L., et al., *Science*, 274:1859–1865, 1996). Transported molecules move through a 100 Å-long channel centered on the molecular 7-fold axis (Song, L., et al., *Science* 274:1859–1865, 1996). The opening of the channel on the cis side of the bilayer (the side of assembly) is ~70 Å above the membrane surface and 29 Å in diameter. The channel widens into a roughly spherical vestibule ~42 Å in diameter. About 20 Å above the membrane plane the vestibule narrows and becomes a 14-stranded β barrel, 52 Å in length, that continues through the membrane averaging about 20 Å in diameter. The trans entrance to the channel lies close to the bilayer surface. Roughly globular molecules of up to ~2000 Da (Krasilnikov, O. V., et al., *FEMS Microbiol. Immunol.* 105:93–100, 1992; Bezrukov, S. M. et al., *Macromolecules* 29:8517–8522, 1996) or elongated polymers of higher mass, such as single stranded nucleic acids (Kasianowicz, J. J., et al., *Proc. Natl. Acad. Sci. USA* 93:13770–13773, 1996) can pass through the αHL pore. The protein is robust; for example, the heptamer is stable at up to 65° C.

It was observed that α-, β- and γ-cyclodextrins (CD) at micromolar concentrations enter the channel and produce reversible partial blocks of the ionic current. In view of this observation, βCD ($M_r$=1135 Da) was examined further. The results of this examination are described more fully in Example 3, below. The block was established when βCD was added from the trans side of a planar bilayer (FIGS. 1a, b) but not from the cis side. The kinetics of the block were consistent with a simple scheme in which there is a single binding site for βCD within the lumen of the channel for which $k^C_{on}$=5.46×10$^4$ M$^{-1}$s$^{-1}$, $k^C_{off}$=1.15×10$^2$ s$^{-1}$, and $K^C_f$= 4.75×10$^2$ M$^{-1}$ in 1 M NaCl, 10 mM Na phosphate and 5 μM EDTA at pH3.0 (trans). The conductance of αHL was 750 pS (SD=21, n=35) in the absence of βCD and 272 pS (SD=9, n=35) in the presence of βCD.

Figure 1C:
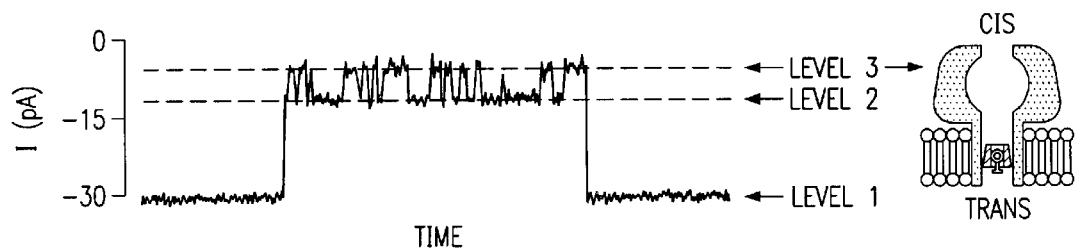
Figure 1D:
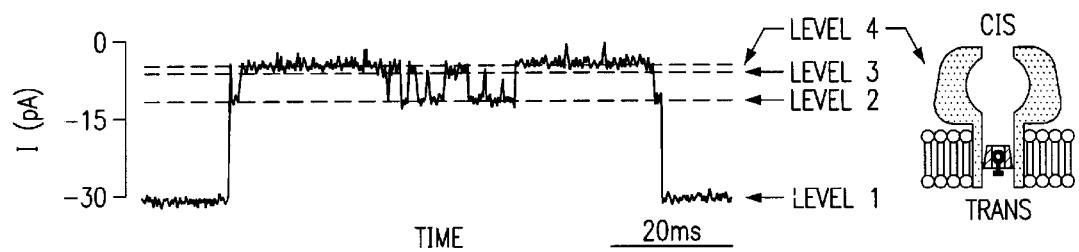

Because the block was partial (64%) and because cyclodextrins are known to act as hosts for a variety of guest molecules, it was postulated that guests might produce further reductions in single channel currents. Indeed, this has been discovered to be the case, as demonstrated in Example 3, below. Specifically, 2-adamantanamine ($A_1$, 80 μM trans) reduced the conductance of the partially blocked channel to 126.5 pS (SD=0.5, n=7) with a residence time ($\tau_{A1}$) of 2.54 msec (SD=0.21), but had no effect on the completely open channel (FIG. 1c). A second guest, 1-adamantanecarboxylic acid ($A_2$, 20 μM trans), also reduced the conductance of the partially blocked channel, this time to 112.2 pS (SD=3.2, n=7) with a residence time ($\tau_{A2}$) of 14.0 msec (SD=0.8). The guests competed for the single binding site in the αHL•βCD complex, so that events due to each could be monitored in a mixture (FIG. 1d). These observations suggested a kinetic scheme and model for the interactions of αHL, βCD and the analytes (FIG. 3).

The kinetic scheme (Scheme 1) suggested by the observations is as follows:

Scheme 1

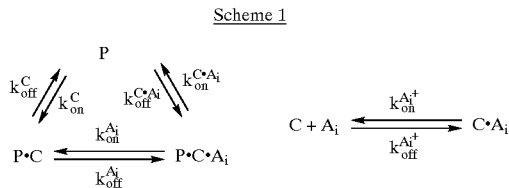

where: P, αHL pore; C, the adapter βCD; $A_i$, guests analytes; C•A, P•C, P•C•$A_i$, the various non-covalent complexes of P, C and $A_i$.

FIG. 2 is a schematic that further illustrates the operation of the system of the present invention. Referring to FIG. 2, the forward and backward rate constants for steps 1, 2 and 3 can be measured by single channel recording. The recording trace reveals both the concentration and identity of the analyte.

More specifically, the host-guest chemistry of the invention involves two mechanisms. In one mechanism, shown in steps 2 and 4 of FIG. 2, the host-guest chemistry uses a "carrier" mechanism whereby the host (carrier) delivers the guest (analyte) to the pore. Alternately, in the "adapter" mechanism shown in FIG. 2, steps 1 and 3, the host (adapter) is lodged in the pore while the guest (analyte) associates and disassociates. Where the residence time of the analyte within the cyclodextrin host is relatively long, the host acts as a carrier rather than an adapter.

Channel modulation occurs only in the presence of the carrier/adapter (host), e.g., cyclodextrin. Detailed studies support the interpretation of FIG. 2. Depending on the analyte and host, transitions associated with 1 and 2, or with 3, can dominate the signal. In either case, a signal that can be interpreted in terms of the concentration and identity of the analyte is obtained. Importantly, the analyte can modulate the single channel conductance while the host is bound and/or modulate the kinetics of the interaction of the host with the channel.

FIGS. 3a–c are molecular graphics diagrams of the model for the interactions of αHL, βCD and the analytes. Specifically, FIGS. 3a–c are three views of a molecular graphics representation of the interaction between αHL and βCD. The structures of αHL were generated from the coordinates (Song, L., et al., *Science* 274:1859–1865, 1996) by using SPOCK 6.3 (Christopher, *SPOCK: the structural properties observation and calculation kit* (*program manual*), Center for Macromolecular Design, Texas A&M University, College Station, Tex., 1998). The βCD structure was generated with Insight II 97.0. The two structures were scaled and superimposed in Adobe Photoshop 4.0. FIG. 3a is a sagittal section view through the heptameric αHL pore showing βCD lodged in the lumen of the transmembrane channel. FIG. 3b is a view into the channel from the trans side with βCD bound. FIG. 3c is a view into the channel from the trans side, βCD removed.

As shown in FIGS. 3a–c, βCD fits snugly into the lumen of the αHL channel with its molecular 7-fold axis parallel to the 7-fold axis of the heptameric pore. A guest molecule, such as an adamantane derivative, can in turn fit within the βCD cavity. Thus, βCD acts as a molecular adapter in a stochastic sensing system where αHL is the sensor element and guest molecules are analytes. The kinetic scheme explains the observed interactions of analytes in simple solutions or in mixtures. In the case of βCD and the adamantane derivatives described here, the residence time of the cyclodextrin in the lumen of the pore is relatively long compared to the residence time of the analyte in the cyclodextrin and βCD acts as an adapter. As noted, where the residence time of the analyte within the cyclodextrin host is relatively long, the host acts as a carrier rather than an adapter.

Figure 4A:
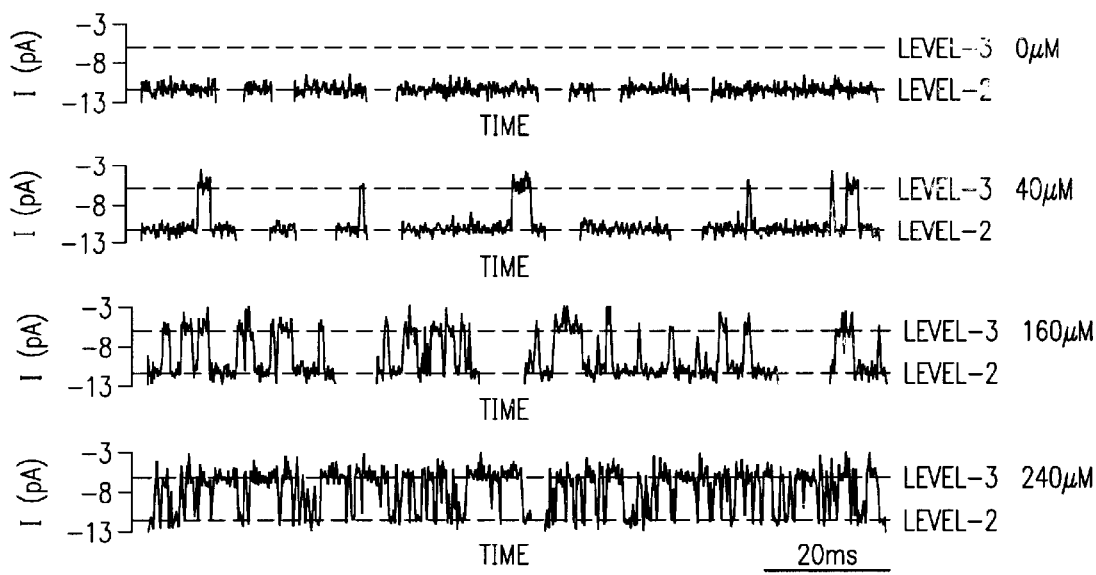
FIG. 4a is a diagram illustrating the response of αHL•βCD at different analyte concentrations.

As described below in Example 5, in the practice of the invention, the signal from an analyte can be used not only to identify the analyte but also to quantitate it. As expected, the frequency of αHL•βCD occupancy by analyte increases with analyte concentration (FIG. 4a). Interestingly, the residence time of βCD•2-adamantanamine on αHL is greater than βCD itself (FIG. 4a), which is true for all βCD•A in this study.

For a single analyte, Scheme 1 gives:

$$P_{P \cdot C \cdot A}/P_{P \cdot C} = K^A_f [A]$$

Figure 4B:
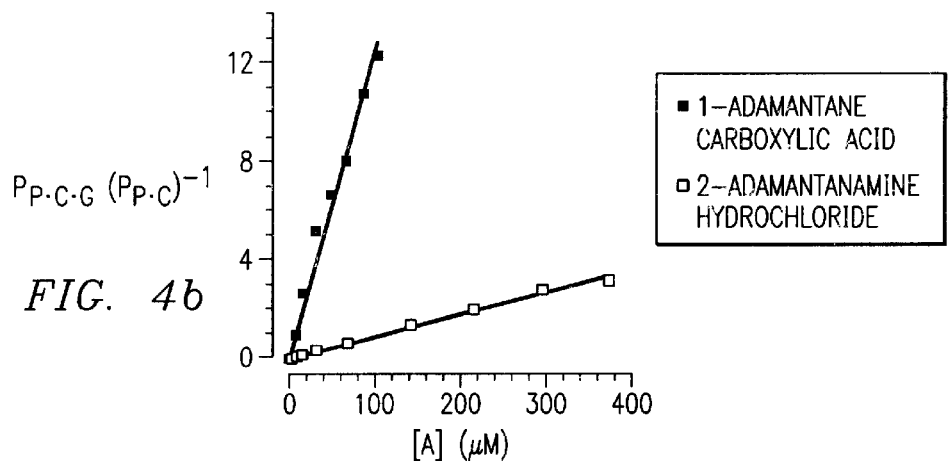
FIG. 4b are plots of $P_{P•C•A}/P_{P•C}$ versus [A] for 2-adamantanamine and 1-adamantanecarboxylic acid.

(see Eq. 10 in Example 7, below) where $P_{P \cdot C \cdot A}$ and $P_{P \cdot C}$ are the experimentally determined probabilities of occurrence of the states of the αHL pore with both βCD and analyte bound or with only βCD bound, $K^A_f$ is the equilibrium formation constant for αHL•βCD•A from analyte (A) and αHL•βCD, and [A] is the concentration of free analyte. [A] can be determined from the experimental values of $P_{P \cdot C}$, $P_P$ ($P_P$ is the probability of occurrence of the unoccupied αHL pore), $[A]_0$ and $[C]_0$ (the total concentrations of analyte and βCD) and $K^C_f$ (the equilibrium formation constant for the αHL•βCD complex), which can be measured separately (see Example 7). Therefore, $K^A_f$ values can be obtained from the slope of a linear plot (FIG. 4b). In this way, $K^A_f$ for 1-adamantanecarboxylic acid and 2-adamantanamine (at pH 3.0) were found to be respectively 1.35±0.19×10$^5$ M$^{-1}$ and 1.03±0.15×10$^4$ M$^{-1}$ (mean ±SD, n=7), corresponding to ΔG values of −7.0 kcal mol$^{-1}$ and −5.5 kcal mol$^{-1}$.

Values of $K^{A'}_f$, the equilibrium formation constant for the analyte (A) with βCD in solution can be obtained from plots of:

$$[C \cdot A] = K^{A'}_f [C][A]$$

(see Eq. 11 in Example 7, below) where values for [C•A], [C] and [A], the concentrations of the βCD•A complex, free βCD and free analyte respectively, can be obtained from experimental or known values of $P_{P \cdot C}$, $P_P$, $[A]_0$, $[C]_0$ and $K^C_f$ (see Example 7). $K^A_f$ values at pH 3.0 for 1-adamantanecarboxylic acid and 2-adamantanamine were found to be respectively 5.76±1.50×10$^4$ M$^{-1}$ and 9.84±2.19×10$^3$ M$^{-1}$, (mean ±SD, n=7), corresponding to ΔG values of −6.5 kcal mol$^{-1}$ and −5.5 kcal mol$^{-1}$, which are closely similar to the values with βCD bound to the αHL pore. Literature ΔG values for 1-adamantanecarboxylic acid binding to βCD, determined by NMR in solution, are in the same range as those determined herein at −7.5 kcal mol$^{-1}$ (pH 4.05) and −6.4 kcal mol$^{-1}$ (pH 7.2) (Rekharsky, M. V., et al., *Chem. Rev.* 98:1875–1917, 1998).

In a working sensor, the total concentration $[A_i]_0$ of analyte $A_i$ of known $K^{A_i}_f$ and $K^{A_i'}_f$ would be determined by the following equation (see Eq. 8 in Example 7, below):

$$[A_i]_0 = \frac{1}{K^{A_i}_f} \cdot \left( \frac{1}{P_{P \cdot C}} + \frac{K^{A_i'}_f}{P_P \cdot K^C_f} \right) \cdot P_{P \cdot C \cdot A_i}$$

Figure 5B:
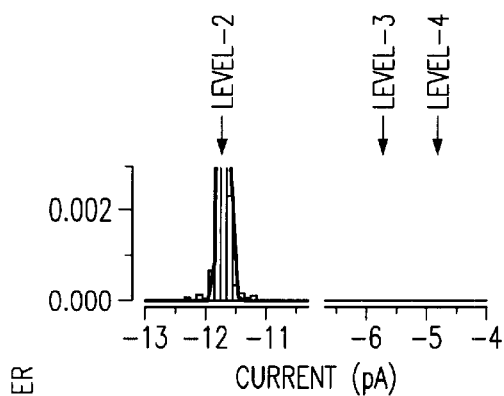
FIG. 5b illustrates the experimentally measured concentrations of $A_1$ and $A_2$, determined from the data in 4a, plotted against the actual concentration of $A_1$.
Figure 5B:
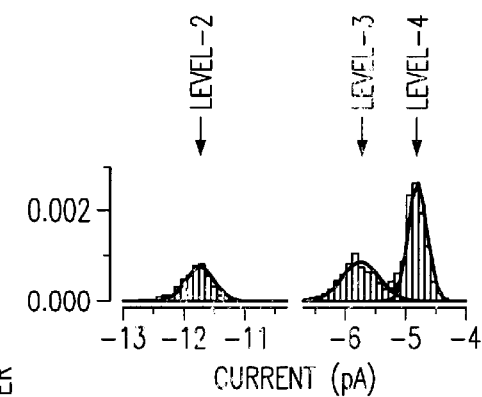
Figure 5B:
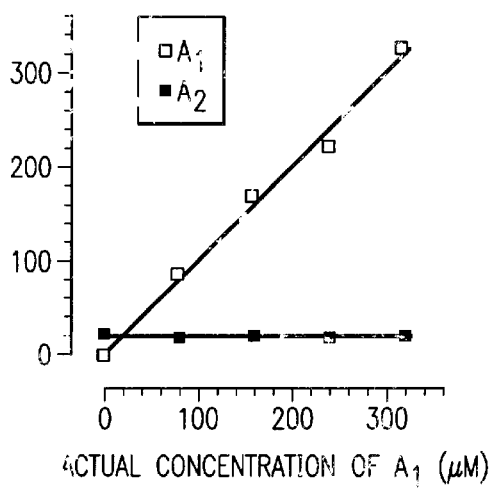

Another important attribute of sensing according to the invention is that two or more analytes, only one of which can occupy the receptor at a given moment, can be identified and quantitated "simultaneously" by a single sensor element. In a mixture, signals from different analytes are recognized by their characteristic extents of channel block and residence times. To illustrate this with αHL and the βCD adapter, an experiment was performed in which 1-adamantanecarboxylic acid ($A_2$) was kept constant at 20 μM, while 2-adamantanamine ($A_1$) was varied. The results are shown below in Example 4. Current amplitude histograms (FIG. 5a), which revealed $P_P$, $P_{P \cdot C}$ and $P_{P \cdot C \cdot A_i}$, and Eq. 8 were used to generate the total concentrations of the two analytes, $[A_1]_0$ and $[A_2]_0$. The values obtained were in close agreement with the actual concentrations in the mixtures (FIG. 5b).

Analyte sensing with adapter molecules provides a highly versatile approach for analyte identification and quantitation. The concept bears some resemblance to olfaction in which carrier molecules (olfactory binding proteins) deliver odorants to membrane-bound receptors (Bianchet, M. A., et al., *Nature Struct. Biol.* 3:934–939, 1996). As in nature, both the adapter/carrier and the receptor may be varied. For example, the range of analytes that can be detected may be extended by using additional naturally occurring and chemically modified cyclodextrins (Rekharsky, M. V., et al., *Chem. Rev.* 98:1875–1917, 1998) as adapters. Additional host molecules that have been developed by synthetic chemists may be considered as adapter/carriers (Chen, H., et al., *Curr. Op. Chem. Biol.* 1:458–466, 1997; Arduini, A., et al., *Curr. Op. Chem. Biol.* 1:467–474, 1997; Beer, P. D., et al., *Curr. Op. Chem. Biol.* 1:475–482, 1997). When necessary, genetically engineered αHL pores (Bayley, H., *Sci. Am.* 277(3):62–67, 1997) or pores other than αHL (Hartgerink, J., D., et al., *Chem. Eur. J.* 4:1367–1372, 1998; Schmid, B., et al., *Protein Sci.* 7:1603–1611, 1998) maybe used to accommodate the alternative adapters, which, as discussed below, may be covalently attached to the pores. Such adapters may covalently attach at the mouth or within the interior of a pore.

In addition to changes in electrical current, various modes of detection, such as those amenable to stochastic sensing with single molecule sensor elements, e.g., fluorescence and force measurements, may be used in the practice of the invention. (Weiss, S., *Science*, 283:1676–1683, 1999; Xie, X. S., et al., *J. Biol. Chem.*, 274:15967–15970, 1999). For example, single molecule fluorescence (Xie, X. S., *Acc. Chem. Res.* 29:598–606, 1996) or force detection methods (Oberhauser, A. F., et al., *Nature* 393:181–185, 1998) may be considered for read-out.

For applications in the field, a rugged version of stochastic sensor elements may be used as was recently achieved for a sensor based on macroscopic channel currents (Cornell, B. A., et al., *Nature* 387:580–583, 1997). Thus, the present invention is not limited to the laboratory bilayer systems as described in the Examples, but also encompasses sensor elements incorporated into more rugged devices for use in the field.

The present invention is a substantial improvement over stochastic sensing using pore proteins as sensor elements without the benefit of an adapter/carrier. The adapter/carrier of the present invention allows interactions between an analyte and a sensor element that would not normally occur (for example, adamantane-1-carboxylic acid itself does not bind to the pore and therefore produces no signal). The adapter/carrier of the present invention can concentrate analyte, even from the vapor phase. The adapter/carrier may mediate the analysis of organic molecules that are normally insoluble in aqueous media. Two or more analyte molecules that interact with an adapter/carrier can be analyzed simultaneously with a single sensor element. The complex signal can be resolved to reveal the concentrations of multiple components in a mixture. In addition, more than one adapter/carrier can be used in combination with a single sensor element.

Analyte sensing using the novel systems of the present invention provides a number of advantages. These include: high sensitivity; rapid response (milliseconds to seconds in the nanomolar concentration range); reversibility; wide dynamic range; both the concentration and identity of an analyte are determined; the sensor element need not be highly selective—each analyte produces a characteristic signal; several analytes can be quantitated concurrently by a single sensor element; lack of simultaneous competition by similar analytes at the single binding site; fouling cannot give a false reading—signal is not characteristic of an analyte; no loss of signal-to-noise at low analyte concentrations; digital output for facile electronic interfacing; and self-calibration and reagentless operation.

As noted, the use of modified cyclodextrins extends the categories of analytes that give a response and also improves the dynamic range of the response. In addition to natural, modified and synthetic cyclodextrins, many different classes of host molecules may be used. The use of genetically engineered pores to produce new interactions of adapters/carriers with pores, to better accommodate various adapters/carriers, and to alter the kinetics of existing interactions can further extend the categories of analytes that can be examined and the dynamic range of the response.

For instance, host molecules other than cyclodextrins, including naturally occurring, synthetic and genetically engineered materials (e.g., peptide polymers, synthetic host molecules, etc.) may be used without departing from the spirit and scope of the invention. In addition to non-covalent adapters (e.g., cyclodextrins and related molecules), adapters may also be covalently attached to the proteins or pores. For example, single poly(ethylene glycol) molecules (PEG's) have been covalently attached to the interior of the αHL pore. Thus, the invention is not limited to cyclodextrins; rather, a wide range of responsive molecules can be used as adapters for sensing purposes, including but not limited to, PEG's (including derivatized PEG's), synthetic polymers other than PEG, oligonucleotides, aptamers, peptide polymers, oligosaccharides, etc.

As with non-covalent adapters/carriers, mutant αHLs may be used to better accommodate the covalent adapters. In addition to αHL, other pore proteins can be used. As with non-covalent adapters, the invention can also be used with alternative sensor elements including enzymes, antibodies, receptors, etc. Therefore, as with non-covalent adapters/carriers, the invention is highly combinatorial.

Analyte sensing according to the invention using host molecules (e.g., both covalent and non-covalent adapters) and sensor elements (e.g., protein pores) is highly combinatorial with respect to analytes, adapters and the proteins that accommodate them. A vast number of host (adapter/carrier) molecules can be used in combination with a vast number of different pores, genetically engineered to accommodate the host molecule. The invention effectively provides a huge tool box of possible adapters and proteins which can be mixed and matched to make a variety of different biosensors. These different biosensor elements can then be combined as desired into an array made up of multiple different biosensors.

Further, analyte delivery according to the invention is not limited to stochastic sensing, but may be applied in other detection modes as well. For example, it can be used in biosensors that rely on multiple channels in a membrane, i.e., it can be used in both the multichannel (macroscopic current) mode and for stochastic sensing.

A wide range of analytes of broad interest can be examined by the adapter approach of the invention. For example, a variety of therapeutic drugs can be recognized and their concentrations determined (Gu, L.-Q., et al., *Nature*, 398:686–690, 1999). Further, cyclodextrins and adapters other than β-cyclodextrin are effective, expanding the range of analytes that can be examined. Remarkably, αHL can be engineered to better secure the adapters. For example, homoheptameric pores of the mutant αHL-M113N bind β-cyclodextrin ~$10^4$ times more tightly than WT homoheptamers (L.-Q. Gu and S. Cheley, unpublished).

With respect to the lipid bilayers used in the practice of the invention, a more stable environment for lipid bilayers may be provided by solid supports (Heyse, S., et al., *Biochim. Biophys. Acta*, 1376:319–338, 1998; Sackmann, E., *Science*, 271:43–48, 1996). Recent work has focused on making defect-free supported bilayers with an aqueous layer between the bilayer and the support to facilitate the incorporation of pores and provide a reservoir of electrolyte (Heyse, S., et al., *Biochim. Biophys. Acta*, 1376:319–338, 1998). Two groups have reported the switching of protein pores in bilayers supported on gold surfaces (Cornell, B. A., et al., *Nature*, 387:580–583, 1997; Stora, T., et al., *Angew. Chem. Int. Ed. Engl.*, 38:389–392, 1999).

Less conventional approaches for accommodating functional protein pores may prove useful. Planar bilayers can be strengthened by the deposition of S layers (the two-dimensional porous crystalline arrays of a single protein that envelop many bacterial species) and remain able to incorporate active αHL pores (Schuster, B., et al., *Biochim. Biophys. Acta*, 1370:280–288, 1998). Active engineered pores may be placed in nanoscale apertures, which can be produced in a variety of materials (Hulteen, J. C., et al., *J. Am. Chem. Soc.*, 120:6603–6604, 1998; Sun, L., et al.,

*Langmuir,* 15:738–741, 1999). The chemistry of the recipient surface could be tailored to make it more compatible with the protein and the protein may be reciprocally engineered.

Accordingly, one embodiment of the invention is directed to a system for sensing at least one analyte in a sample comprising a sensor element and a host molecule. The sensor element has a receptor site. The host molecule, which acts as an adapter or carrier, is configured to interact with both the receptor site of the sensor element and the analyte to produce a detectable signal. When the host molecule functions as an adapter between the analyte and the receptor site, the host molecule may be covalently or non-covalently attached to the receptor site. The sensing may comprise stochastic sensing.

The sensor element may be disposed in a membrane, such as a bilayer. For example, the system may further comprise a bilayer and the sensor element comprises a channel disposed in the bilayer.

In one such embodiment, the system further comprises a bilayer apparatus. The bilayer apparatus may assume any suitable configuration, including rugged devices for use in the field or laboratory devices. The bilayer apparatus comprises a bilayer separating the bilayer apparatus into a first compartment and a second compartment. The sensor element is disposed in the bilayer so that it forms a channel in the bilayer. For example, the sensor element may be disposed in either the first or second or both compartments, i.e., by stirring, so that it forms a channel in the bilayer. The host molecule is disposed (or may be disposed during actual testing for the analyte) in either compartment or both compartments, as required by the application.

For example, referring to FIG. 7c, sensor element 2 forms a pore 4 in bilayer 6 creating a cis side or compartment 8 and a trans side or compartment 10. Host molecule 12 is lodged in pore 4.

As will be clear to those of skill in the art, the operation of the system may be varied without departing from the spirit and scope of the invention. For instance, the sensor element may disposed in the first or second compartment so that it forms a channel in the bilayer and the host molecule may be disposed in the second compartment, the first compartment, or both compartments. In other words, for those adapters that attach non-covalently, the host molecule may be delivered to either or both mouths of the pore (not just the trans side). Likewise, analytes may be delivered to either mouth.

As will further be clear to those of skill in the art, with respect to covalent adapters, in a prefered embodiment, the adapter is attached to the protein (i.e., αHL) before or after assembly of the pore by targeted chemical modification.

Sensing may comprise identifying or quantitating/determining the concentration of the analyte, or both. The host molecule may be a natural, synthetic or modified cyclodextrin, such as βCD or s$_7$βCD. Other suitable hosts which adapt to the receptor site of the sensor element may also be used, including, but not limited to, poly(ethylene glycol) molecules (including derivatized PEG's), synthetic polymers other than PEG, oligonucleotides, aptamers, peptide polymers and oligosaccharides.

The sensor element may be a protein, such as a transmembrane pore, enzyme, antibody or receptor. In a preferred embodiment, the sensor element comprises or functions as a pore, such as a genetically engineered transmembrane protein pore. Preferred sensor elements include α-Hemolysin (αHL) pores, including wild-type α-Hemolysin (αHL) pores and genetically engineered or mutant α-Hemolysin (αHL) pores.

The signal produced by the analyte may be a change in electrical current, such as a change in the magnitude of the current. The signal may comprise the duration of the change in the current. Alternately, the signal may be a change in fluorescence, a change in force, or other unique signal.

The system may be used to sense more than one analyte. Analytes which may be detected include, but are not limited to, organic molecules and molecules lacking a charge.

Another embodiment of the invention is directed to a system for sensing a plurality of different analytes comprising a plurality of different sensor elements, each sensor element comprising a pore and having a receptor site, and a plurality of different host molecules, the host molecules each configured to interact with a receptor site of one of the plurality of different sensor elements and one of the different analytes to produce a detectable signal.

Another embodiment of the invention is directed to a biosensor for detecting an analyte in a sample comprising a bilayer which separates the biosensor into a first compartment and a second compartment, a sensor element disposed in the bilayer so that it forms a channel in the bilayer, and a host molecule. The host molecule is configured to interact with a receptor site on the sensor element and the analyte to produce a detectable signal.

Preferably, the sensor element is disposed in the first compartment and stirred so that it forms a channel in the bilayer, and the host molecule is disposed in either the first or second compartment, or both. In a preferred embodiment, the host molecule is disposed in the second compartment during testing for the analyte, i.e., the host molecule and sample are added to the second compartment substantially simultaneously.

Another embodiment of the invention is directed to a method for sensing at least one analyte in a sample comprising providing a biosensor, the biosensor comprising a sensor element having a receptor site and a host molecule, the host molecule configured to interact with the receptor site of the sensor element and the analyte to produce a detectable signal, allowing the sample to interact with the biosensor to produce a signal, and detecting the signal. Preferably, sensing comprises stochastic sensing. The host molecule may function as an adapter or carrier.

The biosensor may further comprise a bilayer and the sensor element comprises a channel disposed in the bilayer. In one embodiment, the system further comprises a bilayer apparatus which comprises a bilayer separating the apparatus into a first compartment or side and a second compartment or side and the sensor element is disposed in the bilayer so that it forms a channel in the bilayer.

In a preferred method, the sensor element is added to the first compartment and stirred so that it forms a channel in the bilayer and the step of allowing the sample to interact with the biosensor comprises adding the host molecule and the analyte to the first compartment, the second compartment, or both compartments.

Still another embodiment is directed to a method of making a biosensor for detecting an analyte in a sample comprising providing a bilayer apparatus, the bilayer apparatus comprising a bilayer separating the bilayer apparatus into a first compartment and a second compartment, adding a sensor element to the first compartment and stirring, thereby allowing the sensor element to form a channel in the bilayer, and providing a host molecule. The host molecule is configured to interact with a receptor site on the sensor element and the analyte to produce a detectable signal. The method may further comprise the step of adding the host molecule to the first or second compartment, or both. In a preferred embodiment, the host molecule is added to the second compartment substantially simultaneously with the addition of the sample.

Another embodiment is directed to a method for modifying an interactive property of a protein with a second molecule (i.e., how the protein and second molecule interact with each other, if at all). This method comprises the step of modifying the interactive property of the protein by contacting the protein with a third molecule, the third molecule comprising a non-covalent molecular adapter.

In addition to the foregoing, it has also been discovered that synthetic cyclodextrins may be used as host molecules, with a variety of mutant αHLs as sensor elements, to effect ion selectivity of the transmembrane pore. For example, it has been discovered that the charge selectivity of staphylococcal α-hemolysin (αHL) may be manipulated by using two different cyclodextrins as non-covalent molecular adapters. Anion-selective versions of αHL, including the wild-type pore and various mutants, become more anion-selective when β-cyclodextrin (βCD) is lodged within the channel lumen. By contrast, the negatively charged adapter, heptakis-6-sulfato-β-cyclodextrin ($s_7\beta CD$), produces cation selectivity. The cyclodextrin adapters have similar effects when placed in cation-selective mutant αHL pores.

Most probably, hydrated $Cl^-$ ions partition into the central cavity of βCD more readily than $K^+$ ions, while $s_7\beta CD$ introduces a charged ring near the midpoint of the channel lumen and confers cation selectivity through electrostatic interactions. The molecular adapters generate permeability ratios ($P_{K+}/P_{Cl-}$) over a 200-fold range and may be used in the de novo design of membrane channels both for basic studies of ion permeation and for applications in biotechnology.

As noted, the properties of transmembrane channels and pores may be manipulated by cyclic oligosaccharides comprising glucose units (cyclodextrins) which act as molecular adapters for the pore formed by staphylococcal α-hemolysin. Molecules of up to ~2000 Da can be transported through a wide channel in the pore that is centered on the molecular seven-fold axis. Measurements of ionic currents indicate a weak anion selectivity (Menestrina, G., *J. Membrane Biol.*, 90:177–190, 1986).

Cyclodextrins reduce the conductance of the pore by lodging at a point about halfway through the channel, where the diameter is at its narrowest (~14 Å) (Gu, L.-Q., et al., *Nature*, 398:686–690, 1999). Further, channel blockers can bind to a cyclodextrin while it is in the channel. For example, β-cyclodextrin (βCD) reduces the conductance of WT (wild-type) αHL from 658 pS to 240 pS in 1 M NaCl, pH 7.5, and a large variety of organic molecules cause transient channel blockades by binding within the WT-αHL•βCD complex (Gu, L.-Q., et al., *Nature*, 398:686–690, 1999). The results with channel blockers suggest that a substantial fraction of the ionic current flows through the center of the cyclodextrin molecule when it is lodged in the channel lumen.

Surprisingly, it has been discovered that molecular adapters, such as cyclodextrins, can be used to change the charge or ion selectivity of a transmembrane pore, such as an αHL pore. As demonstrated in Examples 9–11, cyclodextrin adapters were shown to produce substantial changes in the charge selectivity of αHL. For example, the WT-αHL pore equipped with an anionic adapter, $s_7\beta CD$, was strongly cation selective ($P_{K+}/P_{Cl-}$=10), while a mutant αHL equipped with unmodified βCD was strongly anion selective ($P_{K+}/P_{Cl-}$=0.05). The direction of the salt gradient had a significant effect on $P_{K+}/P_{Cl-}$ values (Table 2, below), which may be attributed to several causes, including differential screening of charged groups, effects on the conformation of the protein and the onset of multi-ion transport conditions. Nevertheless, the general trends are unaffected by these deviations. The cyclodextrin adapters produced no significant discrimination between cations, as manifest in $P_{K+}/P_{Na+}$ values.

Ion permeation remains one of the most disputatious areas of theoretical biophysics (Andersen, O. S., *J. Gen. Physiol.*, 113:763–764, 1999; Nonner, W., et al., *J. Gen. Physiol.*, 113:773–782, 1999; Miller, C., *J. Gen. Physiol.*, 113:783–787, 1999; Levitt, D. G., *J. Gen. Physiol.*, 113:789–794, 1999). Computational demands place an understanding of permeation beyond present-day exact molecular dynamics simulations (Jakobsson, E., *Methods*, 14:342–351, 1998; Levitt, D. G., *J. Gen. Physiol.*, 113:789–794, 1999). The two major practicable approaches, chemical kinetics and diffusion theory, are rich in adjustable parameters and it is not surprising they "explain" most experimental observations. For example, a permeability ratio of ten amounts to a barrier difference of only 1.4 kcal $mol^{-1}$, which is readily accommodated. Here is an example where the ability to measure far exceeds the ability to compute. Nonetheless, the findings herein are consistent with qualitative notions about selectivity.

Ion selectivity clearly depends to a large extent on the dimensions of a pore and the spatial distribution of charges at the entrance to and within the channel lumen (Hille, B. (1991) *Ionic Channels of Excitable Membranes* (Sinauer, Sunderland, Mass.); Green, W. N., et al., *Ann. Rev. Physiol.*, 53:341–359, 1991; Roux, B., et al., *Science*, 285:100–102, 1999; Lear, J. D., et al., *J. Am. Chem. Soc.*, 119:3212–3217, 1997; Kienker, P. K., et al., *Biophys. J.*, 68:1347–1358, 1995). A "wide pore" with a radius greater than the Debye length (~10 Å in 100 mM salt, ~3 Å at 1000 mM) generally shows weak selectivity because ions in transit interact primarily with water and other ions, rather than with the wall of the lumen (Kienker, P. K., et al., *Biophys. J.*, 68:1347–1358, 1995). In this case, ion selectivities roughly reflect the diffusion coefficients of individual ions in solution. Narrow pores, such as voltage-gated K channels (d=3 Å), Na channels (d=4 Å), and gramicidin A (d=4 Å) are at the opposite extreme and show not only high charge selectivity, but substantial discrimination among ions of the same charge. Here, high selectivity arises through dehydration of ions in the channel lumen and coordination by preorganized functional groups in a selectivity filter (Hille, B. (1991) *Ionic Channels of Excitable Membranes* (Sinauer, Sunderland, Mass.); Eisenman, G., et al., *J. Membr. Biol.*, 76:197–225, 1983), which in the case of K channels are the oxygen atoms of backbone carbonyls (Roux, B., et al., *Science*, 285:100–102, 1999; Doyle, D. A., et al., *Science*, 280:69–77, 1998). Between the extremes of wide and narrow channels, mid-sized channels, such as the nicotinic acetylcholine receptor and the anion-selective GABAa receptor show high charge selectivity, but low selectivity among ions of the same charge. The selectivity of wide and mid-sized channels can be altered by using mutagenesis to place or alter charged amino acid side chains along the conductive pathway and at its entrance (Saxena, K., et al., *Biochemistry*, 38:2206–2212, 1999; Starostin, A. V., et al., *Biochemistry*, 38:6144–6150, 1999; Kellenberger, S., et al., *Proc. Natl. Acad. Sci. USA*, 96:4170–4175, 1999; Kieckmann, G. R., et al., *Biophys. J.*, 76:618–630, 1999)). Even for high selectivity channels electrostatics can provide a prefilter mechanism (Roux, B., et al., *Science*, 285:100–102, 1999; Doyle, D. A., et al., *Science*, 280:69–77, 1998).

WT-αHL should be considered a "wide pore" (Menestrina, G., *J. Membrane Biol.,* 90:177–190, 1986). The narrowest internal diameter is ~14 Å near Met-113, which is close to the cyclodextrin binding site (Gu, L.-Q., et al., *Nature,* 398:686–690, 1999; Song, L., et al., *Science,* 274:1859–1865, 1996). In keeping with the assignment as a wide pore, WT-αHL is of high conductance (658 pS, 1 M NaCl, pH 7.5, −40 mV) and, despite the presence of charged residues throughout the channel lumen (FIG. 7a), charge selectivity is weak (Menestrina, G., *J. Membrane Biol.,* 90:177–190, 1986; under the conditions described herein $P_{K+}/P_{Cl-}=0.55-0.79$).

The selectivity of αHL can be altered by introducing multiple charged side chains into the channel lumen, as seen with αHL-CH1 ($P_{K+}/P_{Cl-}=5.1$; 541 pS, 1 M KCl, pH 7.4, −40 mV), in which the net charge of the lower half of the transmembrane barrel is changed from −7 to −21. WT-αHL and αHL-CH1 pores both bound the neutral adapter βCD, which introduces a mid-sized constriction (internal diameter 6.2 Å (Jeffrey, G. A. & Saenger, W. (1991) in *Hydrogen Bonding in Biological Structures,* eds. Jeffrey, G. A. & Saenger, W. (Springer-Verlag, Berlin Heidelberg), pp. 309–350), still sufficient to admit a hydrated ion) as demonstrated by the reductions in conductance: WT-αHL•βCD, g=240 pS, 1 M NaCl, pH 7.5, −40 mV; αHL-CH1•βCD, g=109 pS, 1 M KCl, pH 7.4, −40 mV. Both pores are anion selective when the adapter is bound. Therefore, the βCD adapter dominates ion selection as judged by the similar outcomes in both an anion-selective and cation-selective backgrounds (Table 2). γCD, which contains eight glucose units, rather than the seven of βCD, is also uncharged, with a larger internal diameter of 7.9 Å (Jeffrey, G. A. & Saenger, W. (1991) in *Hydrogen Bonding in Biological Structures,* eds. Jeffrey, G. A. & Saenger, W. (Springer-Verlag, Berlin Heidelberg), pp. 309–350). As expected, γCD has a lesser effect than βCD on the conductance of the WT-αHL pore (WT-αHL•γCD: g=328 pS, 1 M NaCl, pH 7.5, −40 mV). The influence on anion selectivity was also reduced ($P_{K+}/P_{Cl-}=0.38$).

The seven sulfate groups of $s_7\beta CD$ form a negatively charged ring (−7) (FIG. 7b). This adapter greatly reduced the conductance of the WT-αHL pore: WT-αHL• $s_7\beta CD$, g=53 pS, 1 M NaCl, pH 7.5, −40 mV. Further, the pore became cation selective, $P_{K+}/P_{Cl-}=6.7-10$. In this case, electrostatics predominate over the preference of the interior of the cyclodextrin for anions, in keeping with many studies in the literature in which the introduction of charged rings at channel entrances or in the lumen altered charge selectivity in a qualitatively predictable manner. For example, the mitochondrial voltage-dependent anion channel (VDAC) was made cation selective by point mutagenesis (Blackly-Dyson, E., et al., *Science,* 247:1233–1236, 1990). In general, the placement of negatively charged side chains in the lumen favored cation selectivity, while positively charged side chains favored anion selectivity. The variation in permeability ratios was modest ($P_{K+}/P_{Cl-}$ range 0.6–1.9), as expected of a very high conductance channel (4.5 nS, 1 M KCl, +10 mV). In another case, the porin of Paracoccus denitrificans (g=2.6 nS, 1 M KCl, pH 6, +20 mV) was converted from a weakly anionic form ($P_{K+}/P_{Cl-}=0.35$) to a highly cation selective pore ($P_{K+}/P_{Cl-}=14$) by two Arg->Glu mutations located along the barrel wall at the channel restriction (Saxena, K., et al., *Biochemistry,* 38:2206–2212, 1999). In alamethicin, substitution of a neutral Gln in the channel lumen near the C-terminal entrance with Lys, resulting in six additional charges per active hexamer, converted the cation selective channel ($P_{K+}/P_{Cl-}=4.3$) to an anion selective form ($P_{K+}/P_{Cl-}=0.27$). In all these cases, the lack of a three-dimensional structure does not permit the precise localization of the charged side chains.

Modified cyclodextrins have been used directly as ion channels. For example, Tabushi and colleagues made a β-cyclodextrin carrying hydrophobic chains on four of the seven 6-positions (Tabushi, I., et al., *Tetrahedron Lett.,* 23:4601–4604, 1982). It was claimed that two of these molecule form a transmembrane pore. In a more extensive study, Lehn and collaborators made a "bouquet" molecule from β-cyclodextrin by attaching seven PEG chains to each face. This molecule showed some of the properties expected of a transmembrane pore (Pregel, M. J., et al., *Angew. Chem. Int. Ed. Engl.,* 31:1637–1639, 1992; Pregel, M. J., et al., *J. Chem. Soc. Perkin Trans.,* 2:417–426, 1995). In another study, a condensed monolayer of β-cyclodextrin with all seven 6-positions modified with long alkyl chains was deposited on a graphite electrode. The modified surface was permeant to the electroactive marker p-quinone (Odashima, K., et al., *Analyt. Chem.,* 65:927–936, 1993). Transport through the central cavity was invoked because it could be blocked with guest molecules. Unfortunately, in none of these cases were clear-cut measurements of charge selectivity made.

In sum, the ion selectivity of a transmembrane pore may be modulated using the novel methods disclosed. The adapters can be regarded as crude modular selectivity filters. By reducing the dimensions of the channel lumen from "wide" to "mid-sized," the adapters dominate the charge selectivity of the pore. Unmodified βCD has an affinity for anions, while the negatively charged $s_7\beta CD$ rejects anions, allowing cations to pass in preference. Like site-directed mutagenesis, the adapter approach is versatile because various adapters can be used to program the same protein. Furthermore, mutagenesis and the adapter approach can be combined, for example, to increase the dwell time of the adapter on the protein (Gu, L.-Q., et al., *Nature,* 398:686–690, 1999).

Protein pores with adapters are useful model systems with which to study the details of ion permeation. In the case of the αHL•βCD system, the protein is of known structure and both the protein and the adapter have seven-fold symmetry. The adapter is not likely to produce any major rearrangements of the protein. A similar approach may be used to alter the activity of other proteins, e.g., to modify the active site of an enzyme. Greater pore selectivity may be achieved, for example, by using an adapter with a ring of carbonyl groups similar to those found in the ionophore valinomycin (Duax, W. L., et al., *Biopolymers,* 40:141–155, 1996) or eukaryotic potassium channels (Doyle, D. A., et al., *Science,* 280:69–77, 1998). The control of ion selectivity as disclosed herein may be used in numerous aspects of biotechnology, including drug delivery and biosensor design.

The following examples are offered to illustrate embodiments of the invention, and should not be viewed as limiting the scope of the invention.

EXAMPLES

Example 1

Methods

Unless otherwise indicated, the following methods were used in Examples 2–6.

Pore Formation

Heptameric WT (wild-type) αHL formed by treating monomeric αHL purified from *Staphylococcus aureus* with deoxycholate (Bhakdi, S., et al., *Proc. Natl. Acad. Sci. USA*

78:5475–5479, 1981; Walker, B. J., et al., *J. Biol. Chem.* 267:10902–10909, 1992) was isolated from SDS-polyacrylamide gels as described previously (Braha, O., et al., *Chem. Biol.* 4:497–505, 1997).

Planar Bilayer Recordings

A bilayer of 1,2-diphytanoylphosphatidylcholine (Avanti Polar lipids, Birmingham, Ala., USA) was formed on a 100 to 150 $\mu$m orifice in a 25 $\mu$m thick teflon film (Goodfellow Corporation, Malvern, Pa., USA) separating two compartments (2 ml each) of a planar bilayer apparatus (Montal, M., et al., *Proc. Natl. Acad. Sci. USA* 69:3561–3566, 1972). The solutions in the compartments contained 1 M NaCl, 5 $\mu$M EDTA, 10 mM Na phosphate at pH 7.5 in the cis chamber and pH 3.0 in the trans chamber. Heptameric $\alpha$HL (0.5 to 1 $\mu$l at 0.05 to 0.2 ng/ml) was added to the cis compartment, which was stirred until a single channel inserted into the bilayer. Currents were recorded at a holding potential of –40 mV (cis at ground) by using a patch clamp amplifier (Axopatch 200B, Axon Instruments, Foster City, Calif.). The currents were low-pass filtered with a built-in 4-pole Bessel filter at 5 kHz and sampled at 20 kHz by computer with a Digidata 1200 A/D converter (Axon Instruments). $\beta$CD (Aldrich) and the analytes, i.e., adamantane derivatives (Aldrich) were added to the trans chamber.

Data Analysis

Probabilities and mean durations were analyzed from current amplitude and dwell (residence) time histograms using pClamp 6.0 (Axon Instruments) and are presented using Origin4.1 (Microcal, Northampton, Mass., USA). Measurements are given as the mean ±SD. $P_P$, $P_{P \cdot C}$ and $P_{P \cdot C \cdot A}$ were obtained from the amplitude histograms after fitting the peaks to Gaussian functions.

Example 2
Detection of Single Analyte

FIG. 6 is an example of analyte identification by the carrier technique of the present invention. In this example, the analyte adamantane-1-carboxylic acid is detected by measuring the modulation of the current carried by a single wild-type $\alpha$-hemolysin pore.

Figure 6A:
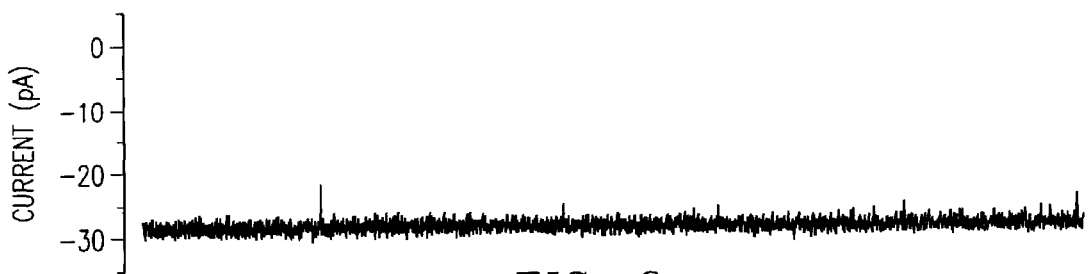
FIG. 6 is a diagram illustrating analyte identification data acquired from operation of the system of the present invention.
Figure 6B:
Figure 6C:
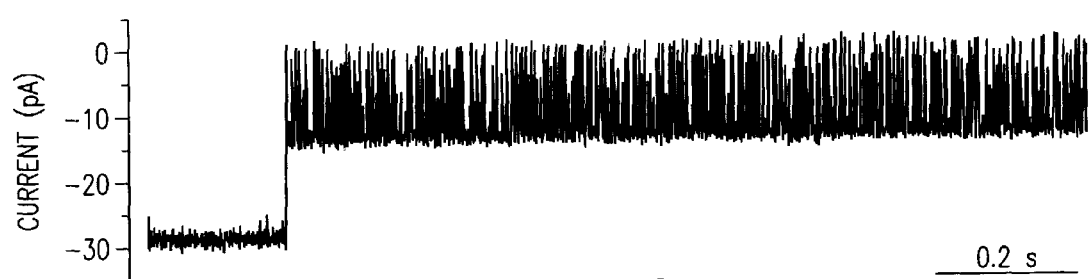

Planar bilayer recordings were made under the following conditions: Buffer 1 M NaCl, 5 $\mu$M EDTA, 10 $\mu$M MOPS, pH 7.5; potential, –40 mV; $\alpha$-hemolysin added to the cis chamber; $\gamma$-cyclodextrin added to the trans chamber; adamantane-1-carboxylic acid added to the trans chamber. FIG. 6a shows a single channel current in the absence of carrier (cyclodextrin) and analyte (adamantane-1-carboxylic acid); FIG. 6b shows step reduction in the current caused by a single carrier (5 $\mu$M) binding event; FIG. 6c shows analyte (20 $\mu$M) binds to the carrier on the pore and modulates the current with a characteristic concentration-dependent signature.

Example 3
Guests (Analytes) on Host Molecule (Adapter) Reduce Single Channel Currents This example demonstrates that guest molecules bound to the host molecule reduced single channel currents.

The results are depicted in FIG. 1, which shows bilayer recordings demonstrating the interaction of a single $\alpha$HL pore with $\beta$CD and the model analytes 2-adamantanamine ($A_1$) and 1-adamantanecarboxylic acid ($A_2$). All traces were recorded at –40 mV (cis at ground). The buffer was 1 M NaCl, 10 mM Na phosphate and 5 $\mu$M EDTA at pH 7.0 (cis) and pH3.0 (trans). $\alpha$HL was added to the cis chamber and $\beta$CD and the adamantane derivatives to the trans chamber. FIG. 1a shows a single $\alpha$HL pore continuously open, –31.5 pA (level 1). FIG. 1b shows that $\beta$CD (20 $\mu$M, trans) produces transient partial blockades of the channel, –11.5 pA (level 2). FIG. 1c shows that 2-adamantanamine (20 $\mu$M, trans) does not affect the fully open channel (level 1), but produces an additional block of $\alpha$HL•$\beta$CD, –5.7 pA (level 3). FIG. 1d shows that 1-adamantanecarboxylic acid (20 $\mu$M, trans) produces additional blockades, –4.7 pA (level 4), of longer duration than those produced by 2-adamantanamine (level 3).

2-adamantanamine ($A_1$, 80 $\mu$M trans) reduced the conductance of the partially blocked channel to 126.5 pS (SD=0.5, n=7) with a residence time ($\tau_{A1}$) of 2.54 msec (SD=0.21), but had no effect on the completely open channel (FIG. 1c). A second guest, 1-adamantanecarboxylic acid ($A_2$, 20 $\mu$M trans), also reduced the conductance of the partially blocked channel, this time to 112.2 pS (SD=3.2, n=7) with a residence time ($\tau_{A2}$) of 14.0 msec (SD=0.8). The guests competed for the single binding site in the $\alpha$HL•$\beta$CD complex, so that events due to each could be monitored in a mixture (FIG. 1d).

Example 4
Interaction of $\alpha$HL•$\beta$CD with Various Substituted Adamantanes Table 1 demonstrates the results of the $\alpha$HL•$\beta$CD interaction with various substituted adamantanes [a].

TABLE 1

| Analyte | $(I_{P \cdot C \cdot A}$ $I_{P \cdot C})/(I_{P \cdot C \cdot A} - I_P)$ [b] | Residence time $(\tau)(ms)$ [c] | $1/K^A_f(\mu M)$ [d] |
|---|---|---|---|
| 1-adamantanecarboxylic acid | 0.346 ± 0.005 | 14.0 ± 0.79 | 7.53 ± 1.16 |
| 2-adamantanamine hydrochloride | 0.286 ± 0.004 | 2.54 ± 0.21 | 98.6 ± 14.28 |
| 1-adamantanamine hydrochloride | 0.294 ± 0.005 | 1.42 ± 0.14 | 109.4 ± 4.95 |
| 1-adamantanecarboxamide | 0.333 ± 0.005 | 3.99 ± 0.18 | 34.2 ± 2.77 |
| 1-adamantanemethanol | 0.352 ± 0.003 | 12.2 ± 1.47 | 15.5 ± 5.26 |
| 1-adamantaneethanol | 0.348 ± 0.003 | 30.6 ± 2.42 | 3.33 ± 1.07 |
| N-(1-adamantyl)-acetamide | 0.348 ± 0.003 | 7.32 ± 2.13 | 14.00 ± 2.24 |

[a] Buffer: 1 M NaCl, 10 mM Na phosphate and 5 $\mu$M EDTA at pH 7.5 (cis) and pH 3.0 (trans). Data was acquired at –40 mV for 2.5 min, n ≥ 3 for all entries.
[b] $I_{P \cdot C \cdot A}$, $I_{P \cdot C}$ and $I_A$ are the current amplitudes of $\alpha$HL with $\beta$CD and analyte bound, $\alpha$HL with only $\beta$CD bound and $\alpha$HL with nothing bound.
[c] The residence time of the analyte on $\alpha$HL·$\beta$CD was obtained by exponential fitting of the dwell (residence)-time histogram.
[d] $K^A_f$ is the equilibrium formation constant for the binding of analyte to $\alpha$HL·$\beta$CD obtained as described in Example 7.

Example 5
Analyte Signals Provide Identifying and Quantitative Data

This example demonstrates that the signal from an analyte can be used not only to identify the analyte but also to quantitate it.

Figure 4C:
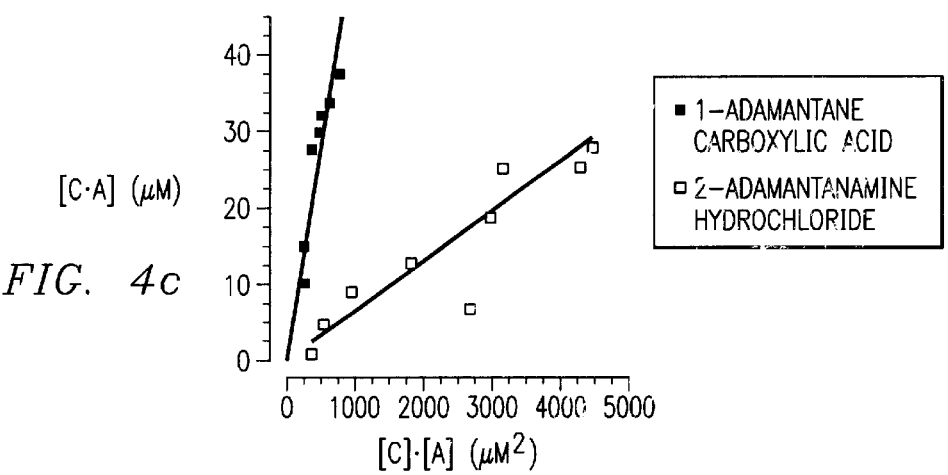
FIG. 4c are plots of [C•A] versus [C]•[A] for 2-adamantanamine and 1-adamantanecarboxylic acid.

Specifically, FIGS. 4a–c illustrate the response of $\alpha$HL•$\beta$CD at different analyte concentrations. FIG. 4a shows the $\alpha$HL•$\beta$CD (level 2) to $\alpha$HL•$\beta$CD•$A_1$ (level 3) transitions at various 2-adamantanamine ($A_1$) concentrations. Representative segments of traces are shown depicting entire $\beta$CD occupancy events at 0, 40, 160 and 240 $\mu$M 2-adamantanamine. The conditions were the same as discussed for Example 3 (FIG. 1), but with 40 $\mu$M $\beta$CD. FIG. 4b shows plots of $P_{P \cdot C \cdot A}/P_{P \cdot C}$ versus [A] for 2-adamantanamine and 1-adamantanecarboxylic acid. The slope yields the formation $K^A_f$ for $\alpha$HL•$\beta$CD•A from analyte and $\alpha$HL•$\beta$CD. FIG. 4c shows plots of [C•A] versus [C][A] for 2-adamantanamine and 1-adamantanecarboxylic acid.

The slope yields the formation $K^A_f$ for βCD•A from analyte and βCD in solution.

As expected, the frequency of αHL•βCD occupancy by analyte increases with analyte concentration (FIG. 4a). The residence time of βCD•2-adamantanamine on αHL is greater than βCD itself (FIG. 4a), which is true for all βCD•A in this study.

Applying Eq. 10 (see Example 7), $K^A_f$ values were obtained from the slope of a linear plot (FIG. 4b). $K^A_f$ for 1-adamantanecarboxylic acid and 2-adamantanamine (at pH 3.0) were found to be respectively $1.35±0.19×10^5$ $M^{-1}$ and $1.03±0.15×10^4$ $M^{-1}$ (mean ±SD, n=7), corresponding to ΔG values of $-7.0$ kcal $mol^{-1}$ and $-5.5$ kcal $mol^{-1}$.

Example 6
Simultaneous Identification and Quantitation of Two Analytes

This example demonstrates the use of sensing using a single sensor element to simultaneously identify and quantitate two or more analytes, only one of which can occupy the receptor at a given moment.

In a mixture, signals from different analytes are recognized by their characteristic extents of channel block and residence times (Table 1). To illustrate this with αHL and the βCD adapter, an experiment was performed in which 1-adamantanecarboxylic acid ($A_2$) was kept constant at 20 μM, while 2-adamantanamine ($A_1$) was varied. Current amplitude histograms (FIG. 5a), which revealed $P_P$, $P_{P•C}$ and $P_{P•C•A_i}$, and Eq. 8 were used to generate the total concentrations of the two analytes, $[A_1]_0$ and $[A_2]_0$. The values obtained were in close agreement with the actual concentrations in the mixtures (FIG. 5b).

Specifically, FIGS. 5a–b illustrate analysis of currents from binary solutions of analytes. FIG. 5a shows current amplitude histograms for a single αHL pore in the presence of βCD and 2-adamantanamine ($A_1$) and 1-adamantanecarboxylic acid ($A_2$). The data has been fitted to Gaussian functions. The peak from unoccupied αHL is not shown. The conditions were the same as in Example 3, FIG. 1, but with 40 μM βCD. The concentrations of the analytes, $A_1$ and $A_2$ respectively, in μM were: a1, 0, 0; a2, 0, 20; a3, 80, 20; a4, 160, 20; a5, 240, 20; a6, 320, 20. As depicted in FIG. 5b, the experimentally measured concentrations of $A_1$ and $A_2$, determined from the data in FIG. 5a, are plotted against the actual concentration of $A_2$.

Example 7
Kinetic Scheme and Related Calculations

The interactions between the αHL pore (P), the cyclodextrin adapter (C) and analyte molecules ($A_i$) may be modeled by the following kinetic scheme (Scheme 1):

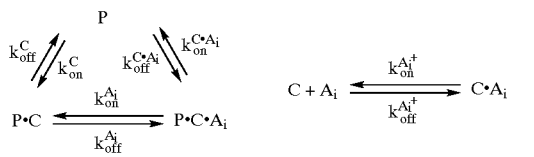

The binding of each analyte molecule ($A_1, A_2, \ldots, A_n$) to the cyclodextrin in solution or the cyclodextrin-pore complex excludes another. Therefore, $$K_f^C = k_{on}^C/k_{off}^C = P_{P•C}/(P_P•[C]) \tag{1}$$

$$K_f^{A_i} = k_{on}^{A_i}/k_{off}^{A_i} = P_{P•C•A_i}/(P_{P•C}•[A_i]) \tag{2}$$

$$K_f^{C•A_i} = k_{on}^{C•A_i}/k_{off}^{C•A_i} = P_{P•C•A_i}/(P_P•[C•A_i]) \tag{3}$$

$$K_f^{A'_i} = k_{on}^{A'_i}/k_{off}^{A'_i} = [C•A_i]/([C]•[A_i]) \tag{4}$$

where $K^C_f$, $K^A_f$, $K^{C•A}_f$ and $K^{A'}_f$ are equilibrium formation constants. $P_P$, $P_{P•C}$ and $P_{P•C•A}$ are probabilities of occurrence of the corresponding states. [C], [A] and [C•A] refer to concentrations of free cyclodextrin, free analyte and the cyclodextrin-analyte complex in solution.

The total concentration of each analyte $[A_i]_0$ is obtained by applying Eq. 4:

$$([A_i])_0 = [A_i] + [C•A_i] \tag{5}$$

$$= [A_i] + K_f^{A'_i}[C][A_i]$$

where $[A_i]$ and $[C]$ are determined by Eq. 2 and Eq. 1:

$$[A_i] = P_{P•C•A_i}/(P_{P•C}•K_f^{A_i}) \tag{6}$$

$$[C] = P_{P•C}/(P_P•K_f^C) \tag{7}$$

Therefore, the total concentration of an analyte can be determined from the expression:

$$([A_i])_0 = \frac{1}{K_f^{A_i}} \cdot \left( \frac{1}{P_{P•C}} + \frac{K_f^{A'_i}}{P_P \cdot K_f^C} \right) \cdot P_{P•C•A_i} \tag{8}$$

Equilibrium Constants

Before using Eq. 8, it is necessary to obtain the equilibrium constants $K^C_f$, $K^A_f$ and $K^{A'}_f$ for each analyte. $K^C_f$ can be obtained by titrating an αHL pore with βCD. $K^C_f$ is the slope of the line obtained by plotting $P_{P•C}/P_P$ versus [C] based on the rearranged form of Eq. 1:

$$P_{P•C}/P_P = K_f^C•[C] \tag{9}$$

$K^A_f$ and $K^{A'}_f$ are obtained from the slopes of plots based on rearranged Eq. 2 and Eq. 4:

$$\frac{P_{P•C•A}}{P_{P•C}} = K_f^A[A] \tag{10}$$

$$[C•A] = K_f^{A'}[C]•[A] \tag{11}$$

where [C•A], [A] and [C]•[A] can be measured by applying Eq. 7:

$$[C•A] = ([C])_0 - [C] = ([C])_0 - \frac{P_{P•C}}{P_P K_f^C} \tag{12}$$

$$[A] = ([A])_0 - [C•A] = ([A])_0 - ([C])_0 + \frac{P_{P•C}}{P_P K_f^C} \tag{13}$$

$$[C] \cdot [A] = \frac{P_{P•C}}{P_P K_f^C} \left( [A]_0 - [C]_0 + \frac{P_{P•C}}{P_P K_f^C} \right) \tag{14}$$

where $[C]_0$ and $[A]_0$ are the total concentrations of carrier and analyte respectively.

Probability Measurement $P_P$, $P_{P•C}$ and $P_{P•C•A}$ are obtained by determining the fractional Gaussian areas corresponding to the relevant states from the amplitude histograms of single channel recording traces. For analytes whose characteristic conductance levels in amplitude histograms are too close to each other to be distinguished, the probability $P_{P \cdot C \cdot A_i}$ can be measured as a fraction of the total binding time $T_i$ of analyte i to the total record time T:

$$P_{P \cdot C \cdot A_i} = T_i/T \qquad (15)$$

Each analyte contributes an exponential component of the residence time (mean residence time is τ) to the total analyte residence (dwell) time distribution F(t):

$$F(t) = \sum \frac{N_i}{\tau_i} e^{-\frac{t}{\tau_i}} \qquad (16)$$

where $N_i$ is the fitting scale factor. The total binding time for each analyte is $$T_i = \int_0^\infty \frac{N_i}{\tau_i} t e^{-\frac{t}{\tau_i}} dt = N_i \cdot \tau_i \qquad (17)$$

Sensitivity

The sensitivity of αHL sensor element to a specific analyte A is defined as the total analyte concentration $[A]_0$ at which $$\frac{P_{P \cdot C \cdot A}}{P_{P \cdot C}} = 1 \qquad (18)$$

when $[C]_0 \to 0$, $[A]=[A]_0$. So in this case, the sensitivity (from Eq. 10) is $$[A]_0 = 1/K_f^A \qquad (19)$$

As will be clear to those of skill in the art, the above calculations may be performed in real time by a built-in microprocessor or any other suitable processing device.

Example 8
Materials, Methods and Permeability Ratio Summary

The following reagents were used in Examples 9–11. β-cyclodextrin was from Aldrich (Milwaukee, Wis.) and γ-cyclodextrin from ACROS (Geel, Belgium). Heptakis-6-sulfato-β-cyclodextrin ($s_7\beta CD$) was prepared as described in Vincent, J. B., et al., *Analyt. Chem.*, 69:4419–4428, 1997. Buffers for planar bilayer recordings contained various concentrations of KCl or NaCl and 10 mM $K_2HPO_4$ or $Na_2HPO_4$ (Sigma, St. Louis, Mo.) in deionized water (Millipore Corp., Bedford, Mass.), and were titrated to pH 7.5 with 391 M HCl (EM Science, Gibbstown, N.J.). Experiments with the mutant αHL-CH1 were done in KCl containing 10 mM K phosphate buffer, pH 7.4, and 5 μM EDTA.

The following proteins were used in Examples 9–11. The mutant αHL genes M113N, M113N/L135N and E111N/K147N were prepared by cassette mutagenesis in the plasmid αHL-RL2 (Cheley, S., et al., *Protein Sci.*, 8:1257–1267, 1999). These constructs contain the following additional changes over WT-αHL: Lys-8->Ala, Val-124->Leu, Gly-130->Ser, Asn-139->Gln, Ile-142->Leu. αHL polypeptides with these mutations behave similarly to WT-αHL in hemolysis assays and in planar bilayer recordings, at the salt concentrations used herein (Cheley, S., et al., *Protein Sci.*, 8:1257–1267, 1999). αHL-CH1 is one of several chimeric proteins that feature a transmembrane domain derived from the protective antigen of anthrax toxin fused to the cap domain of αHL (laboratories of R. J. Collier and H. B., in preparation). Residues 119–140 inclusive of αHL (21 residues) were replaced with 22 residues 302–323 from protective antigen. The register of the β strands in the transmembrane domain is that given by Petosa and colleagues (Petosa, C., et al., *Nature*, 385:833–838, 1997).

Heptameric WT-αHL was formed by treating monomeric αHL, purified from *Staphylococcus aureus*, with deoxycholate (Bhakdi, S., et al., *Proc. Natl. Acad. Sci. USA*, 78:5475–5479, 1981; Walker, B. J., et al., *J. Biol. Chem.*, 267:10902–10909, 1992) and isolated from SDS-polyacrylamide gels as described (Braha, O., et al., *Chem. Biol.*, 4:497–505, 1997). Mutant αHL polypeptides were prepared by coupled in vitro transcription and translation, with an S30 extract from *Escherichia coli* (no. L114A, Promega, Madison, Wis.) (Cheley, S., et al., *Protein Sci.*, 8:1257–1267, 1999). Heptamers were prepared from the mutants by assembly on rabbit red cell membranes, followed by preparative SDS-polyacrylamide gel electrophoresis (Cheley, S., et al., *Protein Sci.*, 8:1257–1267,1999).

Figure 7A:
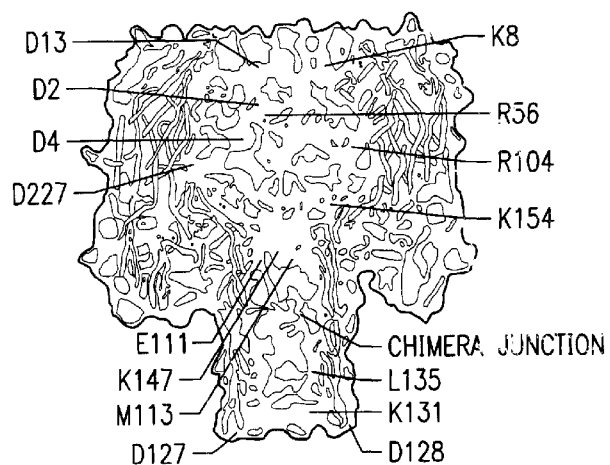
FIG. 7a is a sagittal section through a WT (wild-type) αHL pore.

FIGS. 7a–d depict representations of the proteins and cyclodextrins used in Examples 9–11. FIG. 7a is a sagittal section through the WT-αHL pore showing the location of all the charged side chains in the channel lumen and the key hydrophobic residues M113 and L135. The site of the junction in the chimera αHL-CH1 is indicated. FIG. 7b shows the structures of the β-cyclodextrins used. βCD, R=—OH; $s_7\beta CD$, R=—$OSO_3$—. FIG. 7c is a schematic of the WT-αHL pore used showing βCD lodged in the lumen of the channel. The location is based on mutagenesis data (Gu, L.-Q. et al., *Nature* 398:686–690, 1999). FIG. 7d shows sequences of the transmembrane β barrels in WT-αHL (left) and αHL-CH1 (right).

Bilayer recordings were obtained as follows in Examples 9–11. A 25-μm-thick teflon film (Goodfellow, Malvern, Mass.) with a 100–150 μm diameter orifice was used as the partition between the two chambers (2 ml each) of a teflon bilayer apparatus. The orifice was pretreated with 1:10 hexadecane (Aldrich, Milwaukee, Wis.)/pentane (Burdick & Jackson, Muskegon, Mich.). A solvent-free planar lipid bilayer of 1,2-diphytanoyl-sn-glycero-phosphatidylcholine (Avanti Polar Lipids, Alabaster, Ala.) was formed covering the orifice (Montal, M., et al., *Proc. Natl. Acad. Sci. USA*, 69:3561–3566, 1972; Hanke, W. & Schlue, W.-R. (1993) *Planar Lipid Bilayers* (Academic Press, London)). A potential was applied across the bilayer with Ag/AgCl electrodes with 1.5% agarose (Ultra Pure DNA Grade, Bio-Rad Laboratories, Hercules, Calif.) bridges containing 3 M KCl. Protein was added to the cis chamber, which was at ground.

A positive potential indicates a higher potential in the trans chamber and a positive current is one in which cations flow from the trans to the cis chamber. Single channel currents were recorded with an Axopatch 200B patch-clamp amplifier (Axon Instruments, Inc., Foster City, Calif.) in the whole cell (β=1) mode with a CV-203BU headstage and filtered at 5 kHz with a built-in 4-pole low-pass Bessel Filter. The data were either acquired by computer by using a Digidata 1200 A/D converted (Axon) or stored on DAT tape with a Dagan Unitrade DAS 75 recorder and subsequently transferred to the computer after filtering at 1 kHz through a low-pass 8-pole Bessel filter (Model 900, Frequency Devices, Haverhill, Mass.). The data were acquired by using Clampex 7.0 software (Axon) after sampling at a rate of 20 kHz and analyzed with pClamp 6.03 (Axon) and Origin (Microcal Software Inc., Northampton, Mass.) software.

Experiments were initiated by the addition of heptameric αHL to the cis compartment with stirring until a single channel inserted into the bilayer. For the WT heptamer, oligomerized with deoxycholate, the final concentration was 3–30 ng ml⁻¹. For the mutant heptamers, oligomerized on red cell membranes, the final concentration was ~0.2 ng ml$^{-1}$. βCD or s$_7$βCD was added to the trans chamber to 40 μM. Experiments were at 22±2° C.

Data was analyzed in Examples 9–11 as follows. Single-channel conductances were determined by fitting the peaks in amplitude histograms to Gaussian functions. The permeability ratios (P$_{K+}$/P$_{Cl-}$, P$_{K+}$/P$_{Na+}$) were calculated from reversal potentials by using the GHK equation.

$$\frac{P_{K^+}}{P_{Cl^-}} = \frac{[a_{Cl^-}]_t - [a_{Cl^-}]_c e^{V_r F/RT}}{[a_{K^+}]_t e^{V_r F/RT} - [a_{K^+}]_c} \quad (20)$$

under asymmetrical conditions, $$\frac{P_{K^+}}{P_{Na^+}} = \frac{[a_{Na^+}]_c}{[a_{K^+}]_t} e^{-V_r F/RT} \quad (21)$$

under biionic conditions where V$_r$ is the reversal potential (i.e., the electrical potential giving zero current), a$_X$ is the activity of ion X (Zemaitis, J. F., Clark, D. M., Rafal, M., & Scriver, N. (1986) *Handbook of Aqueous Electrolyte Thermodynamics: Theory and Application* (American Institute of Chemical Engineers, New York, N.Y.)), subscripts c and t represent the cis and trans compartments, and the other symbols have their usual meanings. V$_r$ was obtained by a polynomial fit of the current-voltage (I-V) data near zero current. For asymmetrical conditions, one chamber (cis or trans) contained 1000 mM KCl, while the other chamber contained 200 mM KCl, except for the αHL-CH1 pore where: cis, 1000 mM KCl; trans, 100 mM KCl. For biionic conditions, one chamber contained 1000 MM NaCl and the other 1000 mM KCl. After the measurements, the membrane was broken to determine the contribution of electrode junction potentials. This value was normally smaller than 0.5 mV. Permeability ratios for αHL depend upon several variables including pH and bilayer composition (Krasilnikov. O. V., et al., *J. Membrane Biol.*, 156:157–172, 1997) and the results obtained are valid only for the conditions stated.

Figure 10:
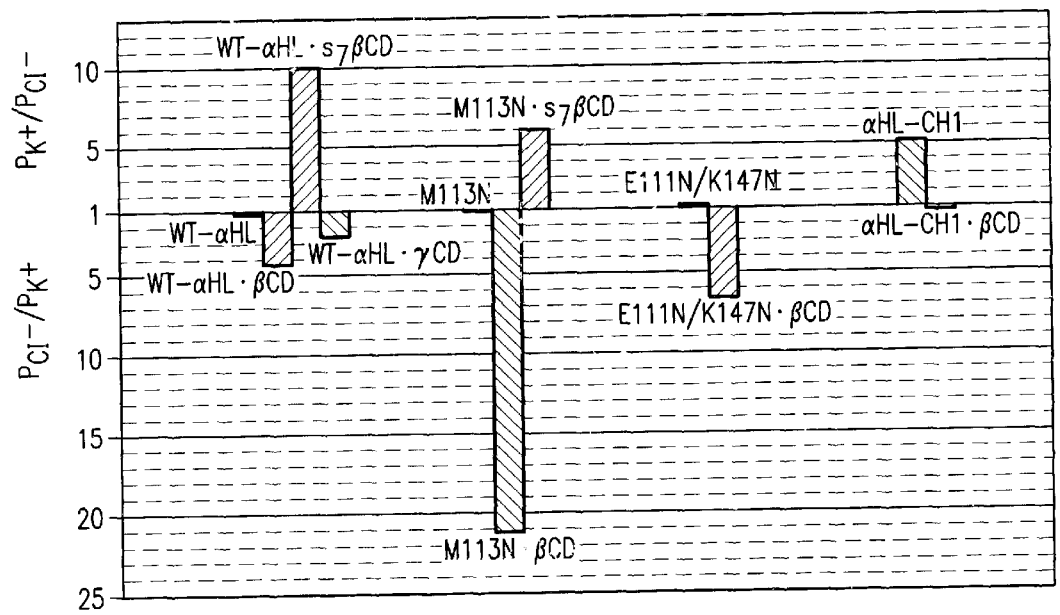
FIG. 10 is a summary of charge selectivity data.

Charge selectivity data is summarized in FIG. 10. For cation selective pores (P$_{K+}$/P$_{Cl-}$) is shown (dark bars). For anion selective pores, the ratios in Table 2 have been inverted to give P$_{Cl-}$/P$_{K+}$ (shaded bars).

Table 2 provides a summary of the permeability ratios (P$_{K+}$/P$_{Cl-}$) and conductance values (g) determined in Examples 9–11 for the various α-hemolysins, with and without adapters, that were evaluated.

Example 9

Cyclodextrins Act as Molecular Adapters to Enhance the Anion Selectivity of αHL Pores Various α-hemolysins and cyclodextrins were used in this example and those which follow (FIG. 7).

As noted, βCD lodges transiently in the lumen of the WT-αHL pore, where it acts as a non-covalent molecular adapter reducing the unitary conductance (Table 2) and serving as a binding site for channel blockers (Gu, L.-Q., et al., *Nature*, 398:686–690, 1999). The homoheptameric WT-αHL pore is weakly anion selective (Menestrina, G., *J. Membrane Biol.*, 90:177–190, 1986).

Figure 8A:
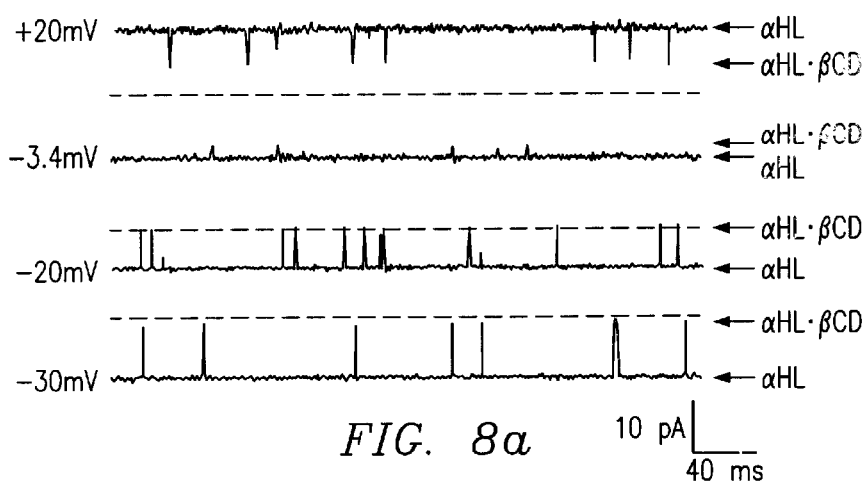
FIG. 8a is a representative bilayer current recording through the WT-αHL pore by cyclodextrin adapters in the presence of 40 μM βCD added to the trans side of the bilayer.

To determine whether the selectivity is altered while βCD is in the channel lumen, single channel currents were recorded under asymmetric conditions: 1000 mM KCl cis, 200 mM KCl trans, pH7.5 (FIG. 8a). Specifically, FIG. 8a shows current recording in the presence of 40 μM βCD added to the trans side of the bilayer. The chambers contained 10 mM K phosphate, pH 7.5, with: cis: 1000 mM KCl; trans: 200 mM KCl. The transmembrane potential is indicated.

Figure 8B:
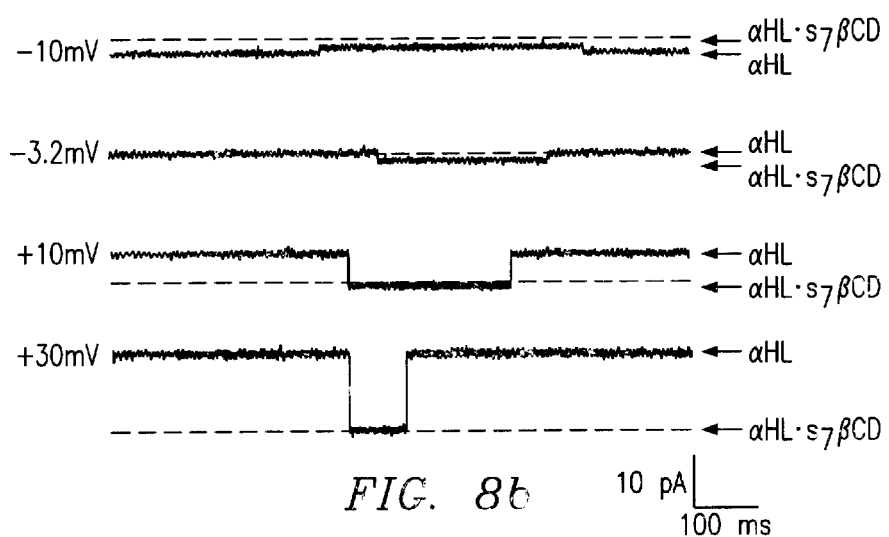
FIG. 8b is a representative bilayer current recording through the WT-βHL pore by cyclodextrin adapters in the presence of 40 μM $s_7βCD$ added to the trans side.
Figure 8C:
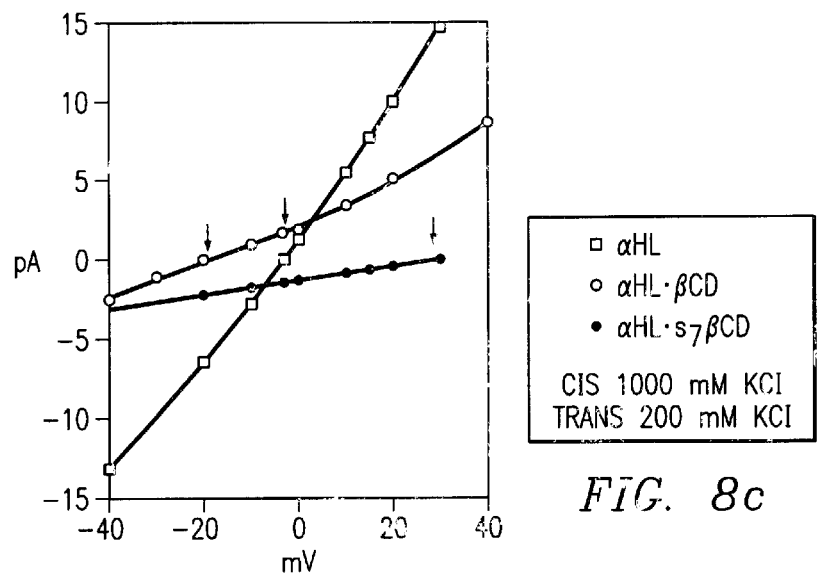
FIG. 8c depicts I-V curves showing modulation of single channel currents through the WT-αHL pore by cyclodextrin adapters, specifically I-V curves for αHL (□), αHL•βCD (○) and αHL•$s_7$βCD (•) based on recordings made with cis: 1000 mM KCl; trans, 200 mM KCl.

I-V curves were plotted for the contributions arising from the unmodified WT-αHL pore and the WT-αHL•βCD complex (FIG. 8c). Specifically, FIG. 8c shows I-V curves for αHL (□), αHL•βCD (○) and αHL•s$_7$βCD (•) based on recordings made with cis: 1000 mM KCl; trans: 200 mM KCl. Reversal potentials (V$_r$) are marked by arrows.

Figure 8D:
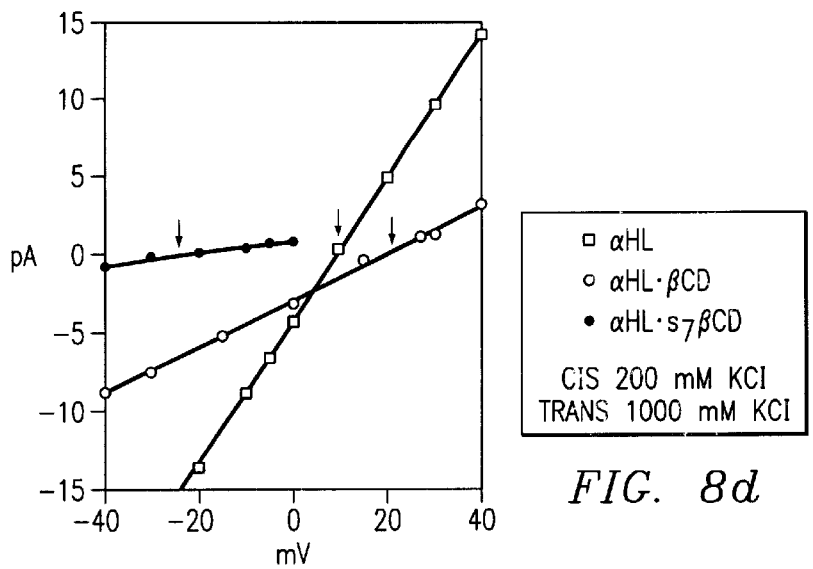
FIG. 8d depicts I-V curves showing modulation of single channel currents through the WT-αHL pore by cyclodextrin adapters, specifically I-V curves for αHL (□), αHL•βCD (○), and αHL•$s_7$βCD (•), based on recordings made with cis: 200 mM KCl; trans, 1000 mM KCl.

Experiments were also performed with the opposite KCl asymmetry: 200 mM KCl cis, 1000 mM KCl trans, pH7.5 (FIG. 8d). Specifically, FIG. 8d shows I-V curves for αHL (□), αHL•s$_7$βCD (•) based on recordings made with cis: 200 mM KCl; trans: 1000 mM KCl. The charge selectivities under the various conditions were then calculated from V$_r$ and Eq. 20. The WT-αHL•βCD complex (P$_{K+}$/P$_{Cl-}$= 0.23–0.25) is significantly more anion selective than the unmodified WT-αHL pore (P$_{K+}$/P$_{Cl-}$=0.55–0.79) (Table 2).

In addition, the effect of βCD on the mutant M113N was examined. M113N binds the cyclodextrin far more tightly than WT-αHL (Gu, L.-Q., et al., *Nature*, 398:686–690, 1999). The almost non-selective M113N pore (P$_{K+}$/P$_{Cl-}$= (0.68–0.87) became highly anion selective with βCD bound (P$_{K+}$/P$_{Cl-}$)=(0.046–0.079) (Table 2). The mutant M113N /L135N (Gu, L.-Q., et al., *Nature*, 398:686–690, 1999) gave similar results. The effect of γ-cyclodextrin, γCD, which contains eight glucose units, on the selectivity of the WT-αHL pore was also tested. γCD enhanced the anion

TABLE 2

| | Charge (e) | Minimum diameter (A) | WT-αHL | | αHL-M113N | | αHL-E111N/K147N | | αHL-CH1 | |
|---|---|---|---|---|---|---|---|---|---|---|
| Adapter | | | P$_{K+}$/P$_{Cl-}$ | g$^a$(pS) | P$_{K+}$/P$_{Cl-}$ | g$^a$(pS) | P$_{K+}$/P$_{Cl-}$ | g$^a$(pS) | P$_{K+}$/P$_{Cl-}$ | g$^b$(pS) |
| None | | 14 | 0.55 ± 0.02$^c$ | 658 ± 11 | 0.68 ± 0.03$^c$ | 622 ± 9 | 1.2 ± 0.1$^d$ | 634 ± 12 | 5.1 ± 0.2$^c$ | 541 ± 11 |
| | | | 0.79 ± 0.02$^c$ | | 0.87 ± 0.04$^c$ | | | | | |
| βCD | 0 | 6.2 | 0.25 ± 0.01$^c$ | 240 ± 5 | 0.079 ± 0.005$^c$ | 261 ± 4 | 0.15 ± 0.02$^d$ | 207 ± 7 | 0.82 ± 0.01$^e$ | 109 ± 9 |
| | | | 0.23 ± 0.01$^d$ | | 0.046 ± 0.006$^d$ | | | | | |
| s$_7$βCD | −7 | <6.2 | 6.7 ± 0.4$^c$ | 53 ± 6 | 4.1 ± 0.2$^c$ | 40 ± 1 | n.d | n.d | n.d. | n.d. |
| | | | 10 ± 0.2$^d$ | | 6.1 ± 0.14$^d$ | | | | | |
| γCD | 0 | 7.9 | 0.38 ± 0.04$^d$ | 328 ± 4 | n.d. | 287 ± 5 | n.d | 275 ± 4 | n.d. | n.d. |

$^a$−40 mV, 1M NaCl, 10 mM Na phosphate, pH 7.5;
$^b$−40 mV, 1M KCl, 10 mM K phosphate, pH 7.4;
$^c$pH 7.5, KCl in mM [cis/trans] was [200/1000];
$^d$pH 7.5, KCl in mM [cis/trans] was [1000/200];
$^e$pH 7.4, KCl mM [cis/trans] was [1000/100].
For each entry, three or more separate experiments were performed and data acquired for at least 1 min. was analyzed. Permeability ratios are quoted as the mean ± s.d.

selectivity of the pore ($P_{K+}/P_{Cl-}$=0.38), but to a lesser extent than βCD ($P_{K+}/P_{Cl-}$=(0.23–0.25)) (Table 2).

Example 10
The Anionic Adapter, Heptakis-6-sulfato-β-cyclodextrin (s₇βCD), Creates a Cation-selective αHL Pore In this example, the effects of a charged adapter on the ion selectivity of αHL were tested. Many commercially available derivatives of βCD are complex mixtures of regioisomers with different extents of substitution. Therefore, a highly purified preparation of heptakis-6-sulfato-β-cyclodextrin (s₇βCD, FIG. 7) was tested.

s₇βCD bound to the WT-αHL pore from the trans side of the membrane produced a substantial single channel block (FIG. 8b; Table 2). Specifically, FIG. 8b shows current recording in the presence of 40 µM s₇βCD added to the trans side. The chambers contained 10 mM K phosphate, pH 7.5, with: cis: 1000 mM KCl; trans: 200 mM KCl. The dwell time of s₇βCD at pH 7.5 (τ=846±37 msec at −40 mV, n=3) was far greater than βCD (τ=0.84 msec±0.09 at −40 mV, n=8) and, as expected, it was voltage-dependent.

I-V curves were constructed for currents recorded under both cis/trans and trans/cis KCl gradients (FIGS. 8c, d) and charge selectivities calculated from $V_r$. Specifically, FIG. 8c shows I-V curves for αHL (□), αHL•βCD (○) and αHL•s₇βCD (•) based on recordings made with cis: 1000 mM KCl; trans: 200 mM KCl. Reversal potentials ($V_r$) are marked by arrows; FIG. 8d shows I-V curves for αHL (□), αHL•s₇βCD (•) based on recordings made with cis: 200 mM KCl; trans: 1000 mM KCl. The WT-αHL•s₇βCD complex is strongly cation selective ($P_{K+}/P_{Cl-}$=6.7–10) (Table 2). αHL-M113N also became cation selective with s₇βCD bound ($P_{K+}/P_{Cl-}$=4.1–6.1) (Table 2).

Figure 8E:
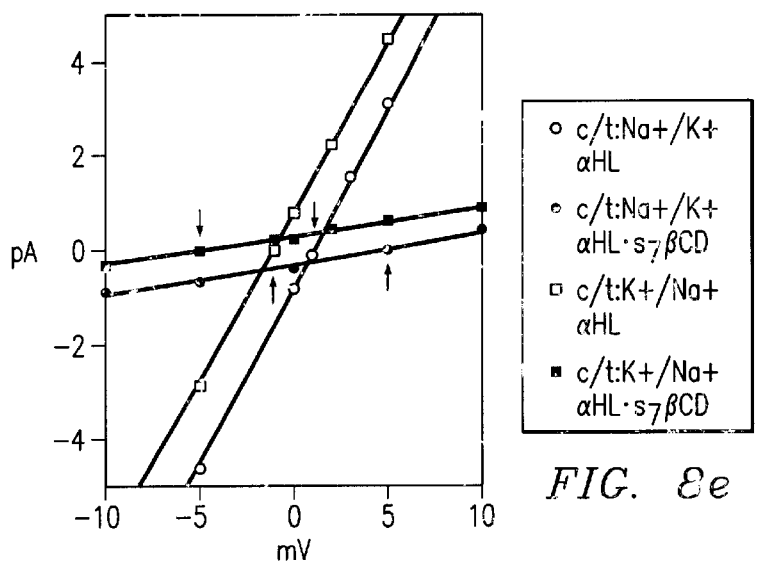
FIG. 8e depicts I-V curves showing modulation of single channel currents through the WT-αHL pore by cyclodextrin adapters, specifically I-V curves under biionic conditions in 10 mM phosphate buffer, pH 7.5: □ and ■, αHL and αHL•$s_7$βCD with cis: 1000 mM KCl; trans, 1000 mM NaCl; ○ and •, αHL and αHL•$s_7$βCD with cis: 1000 mM NaCl; trans, 1000 mM KCl.

The preference of WT-αHL•s₇βCD for Na⁺ and K⁺ was also compared. I-V data were recorded under biionic conditions with 1000 mM NaCl in one chamber and 1000 mM KCl in the other (FIG. 8e). FIG. 8e shows I-V curves under biionic conditions in 10 mM phosphate buffer, pH 7.5: □ and ■, αHL and αHL-s₇βCD with cis: 1000 mM KCl; trans: 1000 mM NaCl; ○ and •, αHL and αHL •s₇βCD with cis: 1000 mM NaCl; trans: 1000 mM KCl. Ion selectivities were calculated from $V_r$ and Eq. 21. The permeability ratio, $P_{K+}/P_{Na+}$=0.92, was the same for both cis/trans and trans/cis buffer gradients. The value for the unmodified WT-αHL pore under the same conditions was $P_{K+}/P_{Na+}$=1.0.

Example 11
Cation-selective Mutant Pores Become Anion Selective with βCD as an Adapter Because the increase in anion selectivity observed when βCD was used as an adapter for the WT-αHL pore was modest, in this example it is determined whether βCD would produce anion selectivity in a cation-selective pore. To this end, αHL-CH1, a chimeric protein that features a transmembrane domain derived from the protective antigen of anthrax toxin fused to the cap domain of αHL, was examined. The net charge per subunit in the transmembrane barrel of homoheptameric αHL-CH1 is −21, compared with −7 in the WT-αHL barrel, and it is cation selective. The altered barrel in αHL-CH1 retains the site near Met-113, where cyclodextrins are believed to bind (Gu, L.-Q., et al., *Nature*, 398:686–690, 1999). Once again, permeability ratios were determined from $V_r$ values (FIGS. 9a, b).

Figure 9A:
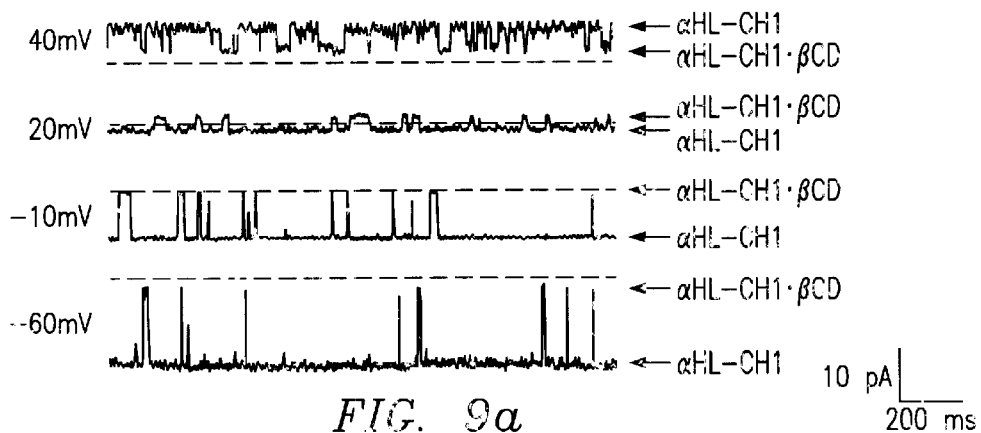
FIG. 9a are bilayer current recordings showing modulation of single channel currents through the αHL-CH1 pore by βCD in the presence of 40 μM βCD added to the trans side of the bilayer.
Figure 9B:
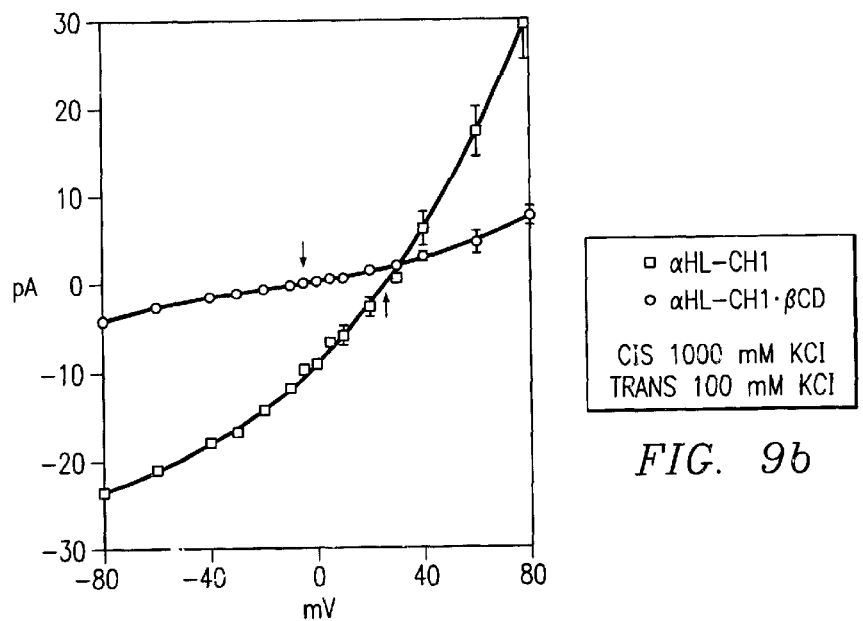
FIG. 9b depicts I-V curves showing modulation of single channel currents through the αHL-CH1 pore by βCD, specifically I-V curves for αHL-CH1 (□) and αHL-CH1•βCD (○) based on recordings made with cis: 1000 mM KCl; trans, 100 mM KCl.

Specifically, FIGS. 9a–b are bilayer recordings and I-V curves showing modulation of single channel currents through the αHL-CH1 pore by βCD. FIG. 9a shows current recording in the presence of 40 µM βCD added to the trans side of the bilayer. The chambers contained 10 mM K phosphate, pH 7.4, containing 5 µM EDTA, with cis: 1000 mM KCl; trans: 100 mM KCl. FIG. 9b shows I-V curves for αHL-CH1 (□) and αHL-CH1•βCD (○) based on recordings made with cis: 1000 mM KCl; trans: 100 mM KCl. The data points represent mean values (±s.d.) from three different experiments for αHL-CH1 and two experiments for αHL-CH1•βCD (Arrows, $V_r$).

βCD indeed converted the cation selectivity of αHL-CH1 ($P_{K+}/P_{Cl-}$=4.4, pH7.4) to weak anion selectivity ($P_{K+}/P_{Cl-}$=0.8) (Table 2). The weakly cation selective mutant E111N/K147N ($P_{K+}/P_{Cl-}$=1.2) was also examined in the presence of βCD, which converted it to an anion selective pore ($P_{K+}/P_{Cl-}$=0.15) (Table 2).

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference, including, but not limited to, U.S. Provisional Patent Application Ser. No. 60/109,034 filed Nov. 18, 1998 and U.S. patent application Ser. No. 09/122,583 filed Jul. 24, 1997. It is intended that the specification and examples be considered exemplary only, with the true scope and spirit of the invention indicated by the following claims.

We claim:

1. A system for sensing at least one analyte in a sample comprising:
   a sensor element having a receptor site; and
   a host molecule, wherein the host molecule interacts with the receptor site of the sensor element and the analyte as an adapter between the analyte and the receptor site so that the sensor element directly produces a detectable signal.

2. A system for sensing a plurality of different analytes comprising:
   at least one sensor element, each sensor element comprising a pore and having a receptor site; and
   a plurality of different host molecules, wherein the host molecules each interact with a receptor site of a sensor element and at least one of the different analytes as an adapter between the analyte and the receptor site so that the sensor element directly produces a detectable signal.

3. A biosensor for detecting an analyte in a sample comprising:
   a bilayer separating the biosensor into a first compartment and a second compartment;
   a sensor element disposed in the bilayer so that it forms a channel in the bilayer; and
   a host molecule, wherein the host molecule interacts with a receptor site on the sensor element and the analyte as an adapter between the analyte and the receptor site so that the sensor element directly produces a detectable signal.

4. A system for sensing at least one analyte in a sample comprising:
   a sensor element having a receptor site; and
   a host molecule, wherein the host molecule interacts with the receptor site of the sensor element and the analyte as a carrier to deliver the analyte to the receptor site so that the sensor element directly produces a detectable signal.

5. A system for sensing a plurality of different analytes comprising:
   a plurality of different sensor elements, each sensor element comprising a pore and having a receptor site; and a plurality of different host molecules, wherein the host molecules each interact with a receptor site of one of the plurality of different sensor elements and one of the different analytes as a carrier to deliver the analyte to the receptor site so that the sensor element directly produces a detectable signal.

6. A biosensor for detecting an analyte in a sample comprising:

a bilayer separating the biosensor into a first compartment and a second compartment;

a sensor element disposed in the bilayer so that it forms a channel in the bilayer; and a host molecule, wherein the host molecule interacts with a receptor site on the sensor element and the analyte as a carrier to deliver the analyte to the receptor site so that the sensor element directly produces a detectable signal.

7. The system of any one of claim 1 or 4 wherein sensing comprises stochastic sensing.

8. The system of claim 1 wherein the host molecule is non-covalently attached to the receptor site.

9. The system of claim 1 wherein the host molecule is covalently attached to the receptor site.

10. The system of any one of claim 1 or 4 wherein the system further comprises a bilayer and the sensor element comprises a channel disposed in the bilayer.

11. The system of any one of claim 1 or 4 wherein the system further comprises a bilayer apparatus, the bilayer apparatus comprising a bilayer separating the bilayer apparatus into a first compartment and a second compartment and wherein the sensor element is disposed in the bilayer so that it forms a channel in the bilayer.

12. The system of claim 11 wherein the sensor element is disposed in the first compartment so that it forms a channel in the bilayer and the host molecule is disposed in the second compartment.

13. The system of claim 11 wherein the sensor element is disposed in the first compartment so that it forms a channel in the bilayer and the host molecule is disposed in the first compartment, the second compartment or both compartments.

14. The system of any one of claim 1 or 4 wherein sensing comprises identifying the analyte.

15. The system of any one of claim 1 or 4 wherein sensing comprises quantitating the analyte.

16. The system of any one of claim 1 or 4 wherein the host molecule is selected from the group consisting of a cyclodextrin, a poly(ethylene glycol) molecule, a synthetic polymer, an oligonucleotide, an aptamer, a peptide polymer and an oligosaccharide.

17. The system of claim 1 wherein the host molecule is a cyclodextrin.

18. The system of claim 17 wherein the cyclodextrin is β-cyclodextrin (βCD).

19. The system of claim 17 wherein the cyclodextrin is $s_7\beta CD$.

20. The system of any one of claim 1 or 4 wherein the sensor element is a protein.

21. The system of claim 20 wherein the protein is selected from the group consisting of a transmembrane pore, an enzyme, an antibody and a receptor.

22. The system of any one of claim 1 or 4 wherein the sensor element comprises a pore.

23. The system of claim 22 wherein the sensor element comprises a genetically engineered transmembrane protein pore.

24. The system of claim 22 wherein the sensor element is an α-Hemolysin (αHL) pore.

25. The system of claim 24 wherein the sensor element is a wild-type α-Hemolysin (αHL) pore.

26. The system of claim 24 wherein the sensor element is a genetically engineered or mutant α-Hemolysin (αHL) pore.

27. The system of any one of claim 1 or 4 wherein the system senses at least two analytes.

28. The system of any one of claim 1 or 4 wherein the signal comprises a change in electrical current.

29. The system of any one of claim 1 or 4 wherein the signal comprises a change in the magnitude and duration of the change in the current.

30. The system of any one of claim 1 or 4 wherein the analyte is an organic molecule.

31. The system of any one of claim 1 or 4 wherein the analyte is not charged.

32. The system of any one of claim 1 or 4 wherein the signal is selected from the group consisting of a change in fluorescence, a change in electrical current and a change in force.

33. The biosensor of any one of claim 3 or 6 wherein the sensor element is disposed in the first compartment so that it forms a channel in the bilayer and the host molecule is disposed in the second compartment.

34. The biosensor of claim 33 wherein the host molecule is disposed in the second compartment substantially simultaneously with the addition of the sample to the second compartment.

35. The biosensor of any one of claim 3 or 6 wherein the sensor element is disposed in the first compartment so that it forms a channel in the bilayer and the host molecule is disposed in the first compartment.

36. The biosensor of claim 35 wherein the host molecule is disposed in the first compartment substantially simultaneously with the addition of the sample to the first compartment.

37. The system of one of claim 2 or 5, wherein the system comprises a plurality of different sensor elements.

38. The system of claim 2, wherein one of more of the host molecules is capable of interacting with one or more of the different analytes as an adapter between the analyte and the receptor site and each interacts with the receptor site of a sensor element and one analyte molecule at a given time.

39. The system of claim 5, wherein one of more of the host molecules is capable of interacting with one or more of the different analytes as a carrier to deliver the analyte to the receptor site and each interacts with the receptor site of a sensor element and one analyte molecule at a given time.

* * * * *

UNITED STATES PATENT AND TRADEMARK OFFICE
CERTIFICATE OF CORRECTION

PATENT NO. : 6,426,231 B1
DATED : July 30, 2002
INVENTOR(S) : Hagan Bayley et al.

It is certified that error appears in the above-identified patent and that said Letters Patent is hereby corrected as shown below:

Column 4,
Line 15, delete "WT-βHL" and insert -- WT-αHL --.

Column 5,
Line 46, after "through a", delete "100 Å-long", and insert -- 100 Å-long --.
Line 49, after "is", delete "~70 Å", and insert -- ~70Å --.
Line 50, delete "29 Å", and insert -- 29Å --.
Line 51, after "vestibule", delete "~42 Å", and insert -- ~42Å -- and after "about", delete "20 Å" and insert -- 20Å --.
Line 53, after "barrel", delete "52 Å", and insert -- 52Å --.
Line 54, after "about", delete "20 Å", and insert --20Å --.

Column 8,
Line 63, delete "maybe" and insert -- may be --.

Column 9,
Line 42, after "selective", delete "—", and insert -- -- --.
Line 46, after "reading", delete "—", and insert -- -- --.

Column 20,
Line 3, delete "$\frac{A_i}{f} = K \frac{A_i}{on}/$" and insert -- $K \frac{A_i}{f} = K \frac{A_i}{on}/$ --.

Lines 13 and 26, delete "$([A_i])_o$" and insert -- $[A_i]_o$ --.
Line 51, after "[C•A]", delete "$([C]_o)$" and insert -- $[C]_o$ --.
Line 54, after "[A]", delete "$([A])_o$" and insert -- $[A]_o$ --.

Column 22,
Line 24, delete "R—OH; $_{s7}\beta CD$, R=—OSO$_3$—" and insert -- R-OH; $_{s7}\beta CD$, R= -OSO$_3$- --.

Column 23,
Table 2, Col. 4, line 2, delete "0.79 ± 0.02[c]" and insert -- 0.79 ± 0.02[d] --.

UNITED STATES PATENT AND TRADEMARK OFFICE
CERTIFICATE OF CORRECTION

PATENT NO. : 6,426,231 B1
DATED : July 30, 2002
INVENTOR(S) : Hagan Bayley et al.

It is certified that error appears in the above-identified patent and that said Letters Patent is hereby corrected as shown below:

Column 27,
Lines 18, 24 and 27, delete "claim", and insert -- claims --.
Line 34, delete claim 12.
Line 38, delete claim 13.
Lines 43, 45, 47 and 58, delete "claim", and insert -- claims --.
Line 52, delete claim 17.
Line 54, delete claim 18.
Line 56, delete claim 19.

Column 28,
Line 1, delete claim 21.
Line 4, delete "claim", and insert -- claims --.
Line 6, delete claim 23.
Line 9, delete claim 24.
Line 11, delete claim 25.
Line 13, delete claim 26.
Lines 15, 17, 19, 22 and 24, delete "claim", and insert -- claims --.
Lines 26, 30 and 38, delete "claim", and insert -- claims --.
Line 34, delete claim 34,
Line 42, delete claim 36.

Signed and Sealed this

Seventeenth Day of June, 2003

JAMES E. ROGAN
*Director of the United States Patent and Trademark Office*